(12) United States Patent
Bhansali et al.

(10) Patent No.: US 10,739,305 B1
(45) Date of Patent: Aug. 11, 2020

(54) BIOSENSING SYSTEMS AND METHODS USING A FET

(71) Applicants: Shekhar Bhansali, Weston, FL (US); Syed Khalid Pasha, Miami, FL (US); Mubarak Ajmuddin Mujawar, Miami, FL (US)

(72) Inventors: Shekhar Bhansali, Weston, FL (US); Syed Khalid Pasha, Miami, FL (US); Mubarak Ajmuddin Mujawar, Miami, FL (US)

(73) Assignee: The Florida International University Board of Trustees, Miami, FL (US)

( * ) Notice: Subject to any disclaimer, the term of this patent is extended or adjusted under 35 U.S.C. 154(b) by 0 days.

(21) Appl. No.: 16/669,621

(22) Filed: Oct. 31, 2019

(51) Int. Cl.
*G01N 27/414* (2006.01)

(52) U.S. Cl.
CPC ............................... *G01N 27/4145* (2013.01)

(58) Field of Classification Search
CPC .................................................. G01N 27/4145
See application file for complete search history.

(56) References Cited

PUBLICATIONS

Parlak, Onur, et al. "Molecularly selective nanoporous membrane-based wearable organic electrochemical device for noninvasive cortisol sensing." Science advances 4.7 (2018).*
Maidin, Nur Nasyifa Mohd, et al. "Interaction of graphene electrolyte gate field-effect transistor for detection of cortisol biomarker." AIP Conference Proceedings. vol. 2045. No. 1. AIP Publishing LLC, 2018.*
Jang, Hyun-June, et al. "Electronic cortisol detection using an antibody-embedded polymer coupled to a field-effect transistor." ACS applied materials & interfaces 10.19 (2018): 16233-16237.*

* cited by examiner

*Primary Examiner* — Robert J Eom
(74) *Attorney, Agent, or Firm* — Saliwanchik, Lloyd & Eisenschenk

(57) ABSTRACT

Systems and methods for sensing analytes using an extended gate field effect transistor (EGFET) are provided. A biosensing system can utilize a biodetection layer on a substrate, which can be coupled to a field effect transistor (FET). The coupling can be such that the gate of the field effect transistor is connected to the substrate having the biodetection layer thereon. The functionalized substrate can include a well-defined area that can hold a specific, pre-determined volume of fluid on top of it. An external electrode can be dipped in the fluid and can then be connected to a power source supplying a gate voltage. The presence or concentration of the target analyte in the fluid can be determined based on the source-drain characteristics of the FET.

18 Claims, 13 Drawing Sheets

US 10,739,305 B1

BIOSENSING SYSTEMS AND METHODS USING A FET

GOVERNMENT SUPPORT

This invention was made with government support under Award Number 1827682 awarded by the National Science Foundation (NSF). The government has certain rights in the invention.

BACKGROUND

Cortisol is produced in the adrenal glands and released into the blood stream of the body in response to stress. While everyone copes with stress differently, any high level of stress and overproduction of cortisol can lead to dangerous side effects including high blood pressure, severe fatigue, severe anxiety, and even depression. Excess production of cortisol is also linked to stress disorders, such as insomnia, Cushing's syndrome, and Post Traumatic Stress Disorder (PTSD). Depending on a person's pattern of activity, cortisol production may differ throughout the day. Typically, an individual who wakes up in the morning to work has the highest production of cortisol in the morning and lowest at night; this trend reverses if the individual has more rest in the morning and works late at night. Hence, continuous monitoring and point of care (POC) testing is the most optimal way to get the most accurate results for different patients.

As it stands now, patients must go out of their way and provide a sample to a clinic or laboratory. In addition, patients must wait a long time for samples to get processed and to receive result. This is detrimental because production levels of cortisol differ for each individual and sex throughout the day, meaning there can be inaccuracies in the results. POC testing is therefore important for personalized diagnosis and treatment.

Currently, a cortisol level from a sample can be detected using immunoassay chromatography, like enzyme-linked immunosorbent assay (ELISA). An electrochemical technique, cyclic voltammetry, is also used for characterization of cortisol in a sample. The systems used in these laboratories to detect the concentration of cortisol are bulky, expensive, time consuming, and require training to operate. As a result, patients don't have access to real-time, continuous monitoring or POC testing for cortisol. Similar problems exist in testing for many other analytes.

BRIEF SUMMARY

Embodiments of the subject invention provide advantageous systems and methods for sensing analytes (e.g., biological analytes) using an extended gate field effect transistor (EGFET). A biosensing system can utilize a biodetection layer (e.g., a synthetic biodetection layer) on a substrate (e.g., a conductive substrate), which can be coupled to a field effect transistor (FET). The method of coupling can be such that the gate of the field effect transistor is connected to the substrate having the synthetic biodetection layer thereon. The functionalized substrate can include a well-defined area (e.g., a well or a flat area) that can hold a specific, predetermined volume of fluid (e.g., liquid) on top of it. An external electrode can be dipped in the fluid and can then be connected to a power source supplying a voltage, which can be the gate voltage. The variations in the charge transfer from the external electrode to the gate electrode of the FET due to the presence of target molecules on the synthetic biodetection layer modulates the source to drain characteristics of the FET. These modulations can be then correlated to the concentration of the target analyte (e.g., based on an already known correlation due to a prior calibration or the like) that is present on the detection layer. Such a biosensing system offers many advantages, including a direct sensing output that can be correlated to the concentration of the target/analyte molecules in terms of the output current of the FET. In addition, this configuration allows for the isolation of the sensitive electronic components from the potentially corrosive environment of the fluids used for sensing (i.e., FET components are isolated from the fluid containing the analyte).

In an embodiment, a biosensing system for detecting a target biological analyte can comprise: an FET comprising a gate, a source, and a drain; an extended gate comprising a conductive substrate in electrical contact with the gate of the FET; and an external electrode that is not attached to the FET or the extended gate, configured to apply a gate voltage to a fluid disposed on a predefined area of the conductive substrate. The conductive substrate can be an MIP that is specifically functionalized for the target biological analyte. The system can further comprise a screen printed carbon electrode (SPCE) disposed on the conductive substrate, the SPCE comprising a reference electrode and a working electrode. The external electrode can be connected to a gate voltage source, the gate voltage source can be connected to the reference electrode of the SPCE, and the gate of the FET can be connected to the working electrode of the SPCE. The drain of the FET can be connected to a drain voltage source with the source of the FET being grounded, or alternatively the source of the FET can be connected to a source voltage source with the drain of the FET being grounded. The predefined area of the conductive substrate can comprise a well in the conductive substrate configured to receive the fluid or a flat area on an upper surface of the conductive substrate designed to receive the fluid. The system can further comprise a small current amplifier in operable communication with the FET, and a microcontroller in operable communication with the small current amplifier; the microcontroller can be configured to receive a source-drain characteristic and determine a concentration of the target biological analyte based on the source-drain characteristic, and the source-drain characteristic can be a source-drain current, a source-drain voltage, or both In another embodiment, a method of sensing a concentration of a target biological analyte can comprise: providing a fluid comprising the target biological analyte to an extended gate comprising a conductive substrate in electrical contact with the gate of an FET, the FET comprising the gate, a source, and a drain; dipping an external electrode, which is not attached to the FET or the extended gate, in the fluid; providing a gate voltage to the external electrode via a gate voltage source connected to the external electrode; analyzing, by a controller in operable communication with the FET, a source-drain characteristic of the FET while the gate voltage is provided to the external electrode; and determining the concentration of the target biological molecule based on the source-drain characteristic of the FET. The source-drain characteristic can be a source-drain current, a source-drain voltage, or both.

DETAILED DESCRIPTION

Embodiments of the subject invention provide advantageous systems and methods for sensing analytes (e.g., biological analytes) using an extended gate field effect transistor (EGFET). A biosensing system can utilize a biodetection layer (e.g., a synthetic biodetection layer) on a substrate (e.g., a conductive substrate), which can be coupled to a field effect transistor (FET). The method of coupling can be such that the gate of the field effect transistor is connected to the substrate having the synthetic biodetection layer thereon. The functionalized substrate can include a well-defined area (e.g., a well or a flat area) that can hold a specific, predetermined volume of fluid (e.g., liquid) on top of it. An external electrode can be dipped in the fluid and can then be connected to a power source supplying a voltage, which can be the gate voltage. The variations in the charge transfer from the external electrode to the gate electrode of the FET due to the presence of target molecules on the synthetic biodetection layer modulates the source to drain characteristics of the FET. These modulations can be then correlated to the concentration of the target analyte (e.g., based on an already known correlation due to a prior calibration or the like) that is present on the detection layer. Such a biosensing system offers many advantages, including a direct sensing output that can be correlated to the concentration of the target/analyte molecules in terms of the output current of the FET. In addition, this configuration allows for the isolation of the sensitive electronic components from the potentially corrosive environment of the fluids used for sensing (i.e., the FET components are isolated from the fluid containing the analyte).

Figure 1:
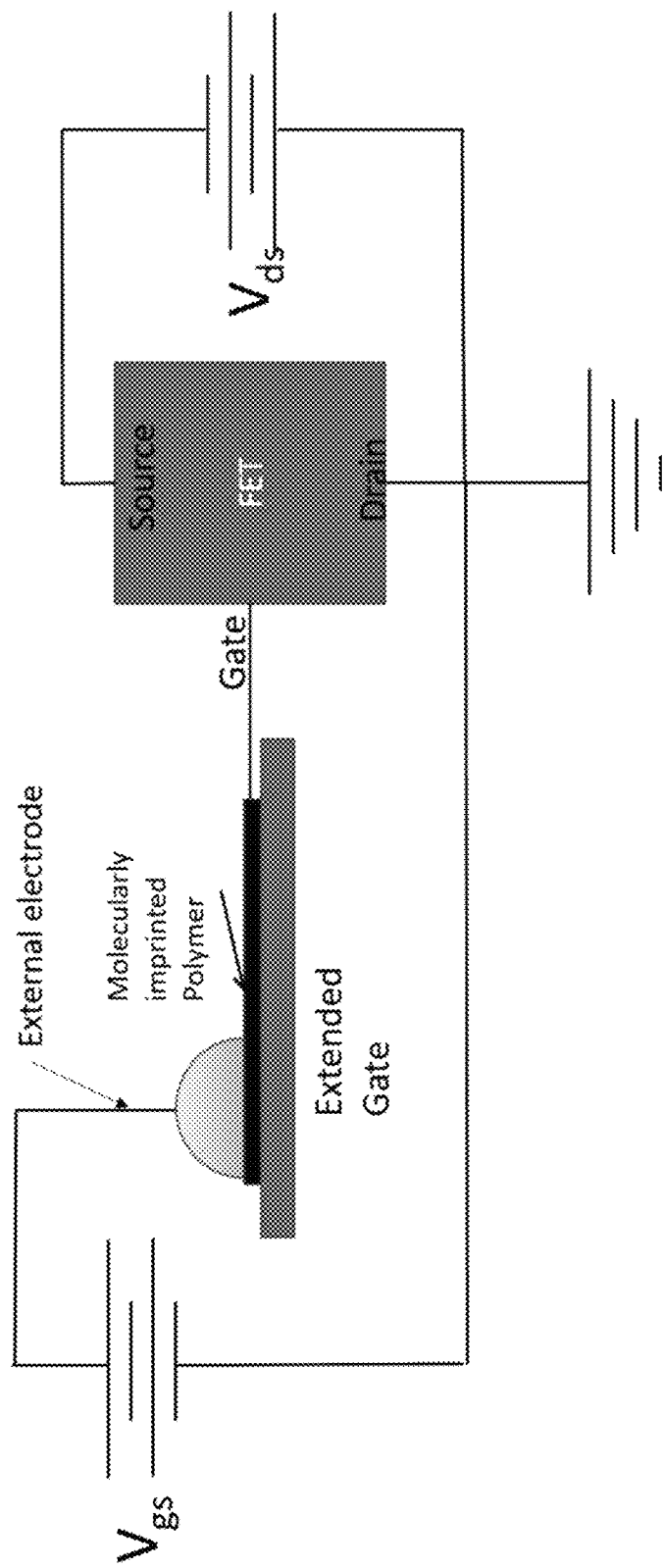
FIG. 1 shows a schematic view of a biosensing system according to an embodiment of the subject invention.

In many embodiments, a molecular imprinted polymer (MIP) (e.g., a polypyrrole-based MIP) can be used as the biodetection layer, or as at least part of the biodetection layer. MIPs are discussed in detail in Manickam et al. (P. Manickam, S. K. Pasha, S. A. Snipes, and S. Bhansali, "A Reusable Electrochemical Biosensor for Monitoring of Small Molecules (Cortisol) Using Molecularly Imprinted Polymers," J. Electrochem. Soc., vol. 164, no. 2, pp. B54-B59, 2017), which is a prior work of the inventors and is hereby incorporated herein by reference in its entirety. The MIP can either be conductive and can be connected to the gate of the FET sensor, as shown in FIG. 1.

Electrochemical (EC)/electrical (e.g., FET, chemiresistive) sensors demonstrate good sensing performance (for a wide variety of analytes including but not limited to cortisol), can be made label-free, can be micro-fabricated, can provide fast results, and are suitable for miniaturization. Electrochemical sensing platforms (e.g., EC cortisol sensing platforms) can be integrated into a point of care (POC) system for continuous monitoring (e.g., online continuous monitoring) of cortisol as a function of one's environment. These systems are crucial for the detection of a targeted analyte outside controlled environments of diagnostic labs and hospitals and have a major impact on the applications of personal care, health, food, and environmental monitoring. An ideal POC biosensor device allows real-time, rapid, label-free, and multiplexed detection with high selectivity and sensitivity. Several challenges do exist in implementing POC sensors. The requirement of redox media for EC sensing adds to design complication for POC devices. The lack of robustness due to the temperature sensitivity of detection molecules (e.g., antibodies, enzymes) pose logistical challenges involving increased costs associated with storage at temperatures below 0° C. The complexity of the electronic system associated with these devices also inhibits or prevents them from being miniaturized for POC applications. Embodiments of the subject invention address these challenges.

A field effect transistor (FET) is active semiconductor device that modulates the flow of the drain current according to the applied charge on the gate electrode. Equation 1 below expresses the magnitude of drain current of a FET with respect to different parameters.

$$I_d = \beta \left( V_{gs} - V_T - \frac{1}{2} V_{ds} \right) V_{ds} I_d \tag{1}$$

where $V_T$ is the threshold voltage. The threshold voltage is the value of $V_{gs}$ beyond which the narrow conduction channel starts forming. $\beta$ is the trans-conductance parameter as expressed in Equation 2.

$$\beta = \mu C_{ox} \frac{W}{L} \tag{2}$$

$\beta$ is a function of the mobility of the electrons ($\mu$) in the inversion layer, the gate insulator capacitance per area ($C_{ox}$) and the channel width to length ratio (W/L).

The property of FETs in which drain currents being modulated due to the presence of charge on the gate surface can be utilized for electrophysiological applications resulting in a sensor. Immobilization of bio-functionalized moieties on the surface of the gate causes a change in the capacitance. This, in turn, modulates the drain current of the FET resulting in a configuration called an Ion Sensitive FET (ISFET). ISFETs can be used as biosensors due to fast response time, high sensitivity, batch processing, and the possibility of integrating on a single chip. However, this configuration can destroy the device due to the often harsh chemical nature of the electrolytes used. The open gate configuration also exposes the device to electromagnetic interference that can result in noisy data. Embodiments of the subject invention address these problems with ISFETs by using an extended gate.

Figure 12:
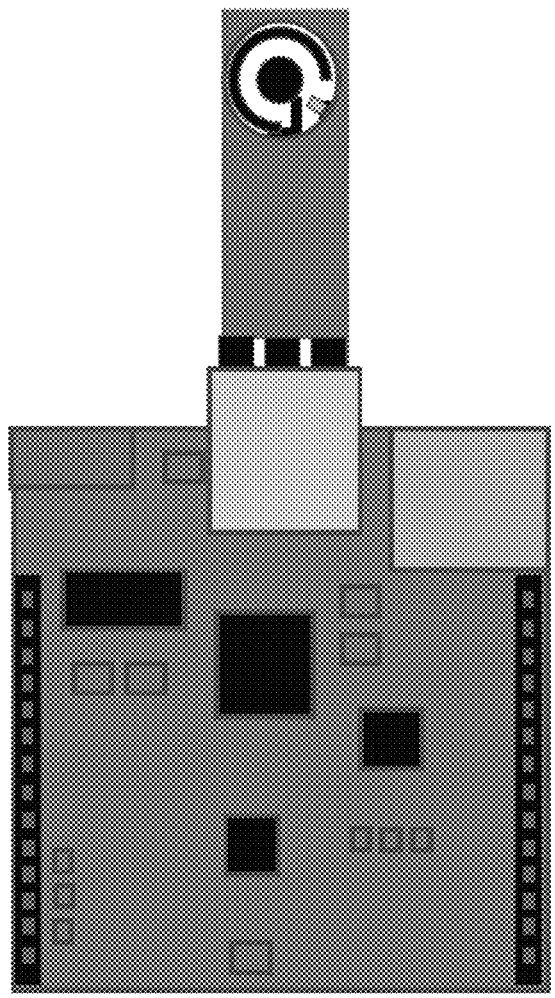
FIG. 12 shows a top view of a biosensing system according to an embodiment of the subject invention.

Systems and method of embodiments of the subject invention circumvent the problems discussed in the previous paragraph by using an extended gate FET (EGFET) to isolate the chemical environment from the FET itself. Referring to FIG. 1, in an embodiment, a system can include an external functionalized substrate that is connected to the gate of the FET. The FET also includes a source and a drain, along with the insulator and gate electrode of the gate. The external electrode can touches the electrolyte, and a gate voltage is applied across the external electrode. The interaction between the ions present in the electrolyte and the functional group present on the extended gate substrate causes a surface potential change. This change of potential causes a change in the flow of current to the gate of the FET. In turn, the gate current modulates the drain-source current in the FET. The modulation of drain current due to the presence of biomolecules on the surface of the extended gate makes it possible to use the FET as a biosensor. This configuration allows for the stabilization of FET output by isolating it from changes happening due to pH, optical variations, and temperature variations because the gate material is not directly exposed to the environment or the chemicals. Although sensing of cortisol is discussed extensively herein, this is for exemplary purposes only and systems and method of embodiments of the subject invention can be used to sense any suitable analyte. FIG. 12 also shows a biosensing system according to an embodiment of the subject invention. Referring to FIG. 12, a top view is shown and integrated electronics (lower section of figure) can be seen as well, allowing for a portable format. The top portion of the figure shows the extended gate in contact with the FET.

Figure 13:
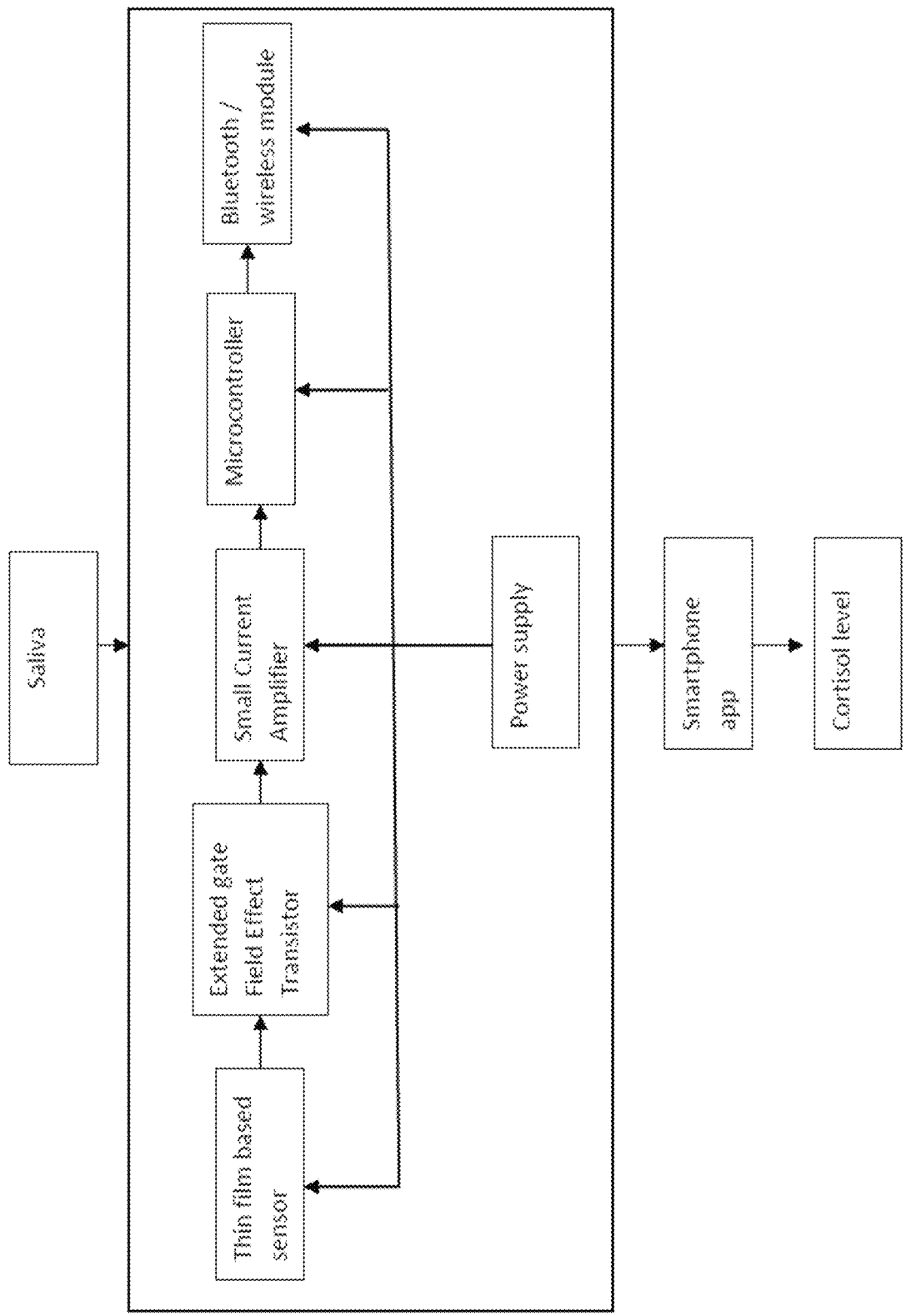
FIG. 13 shows a block diagram view of a biosensing system/method according to an embodiment of the subject invention.
Figure 1:
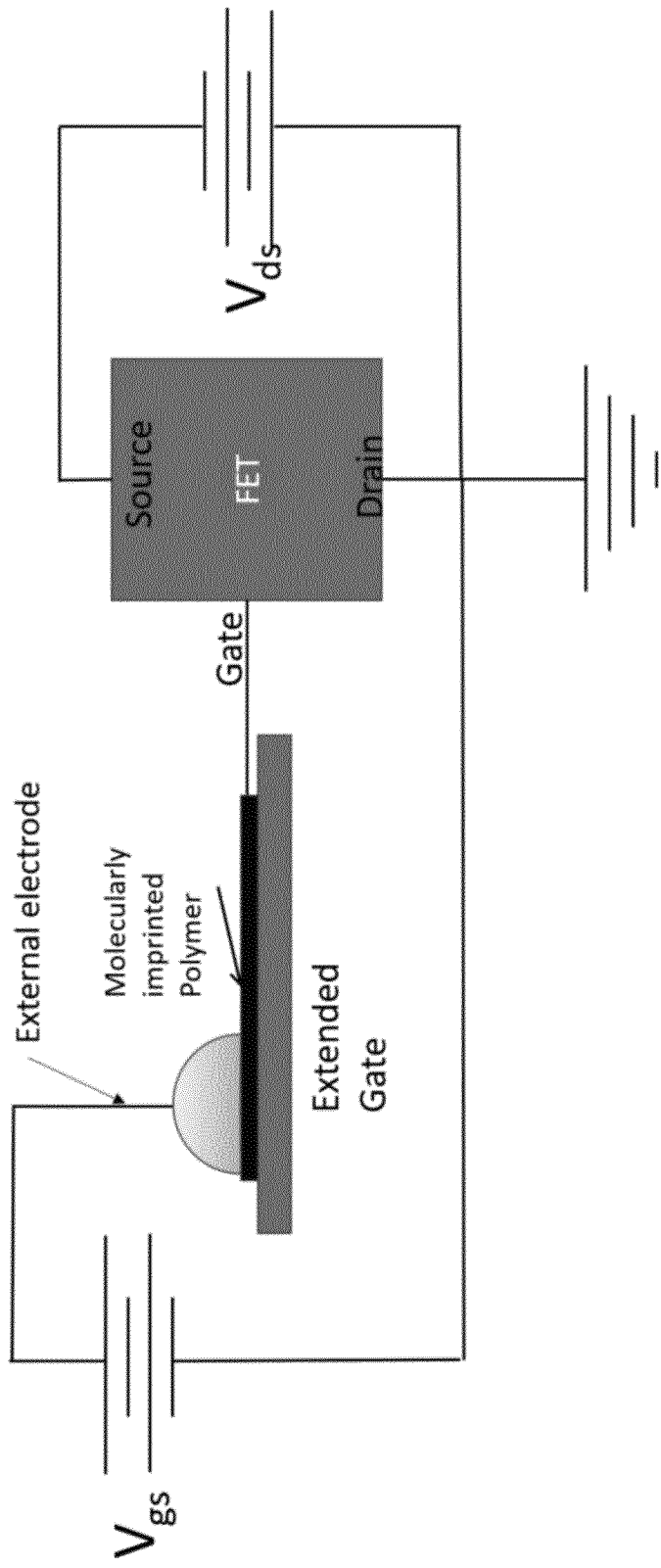
Figure 2:
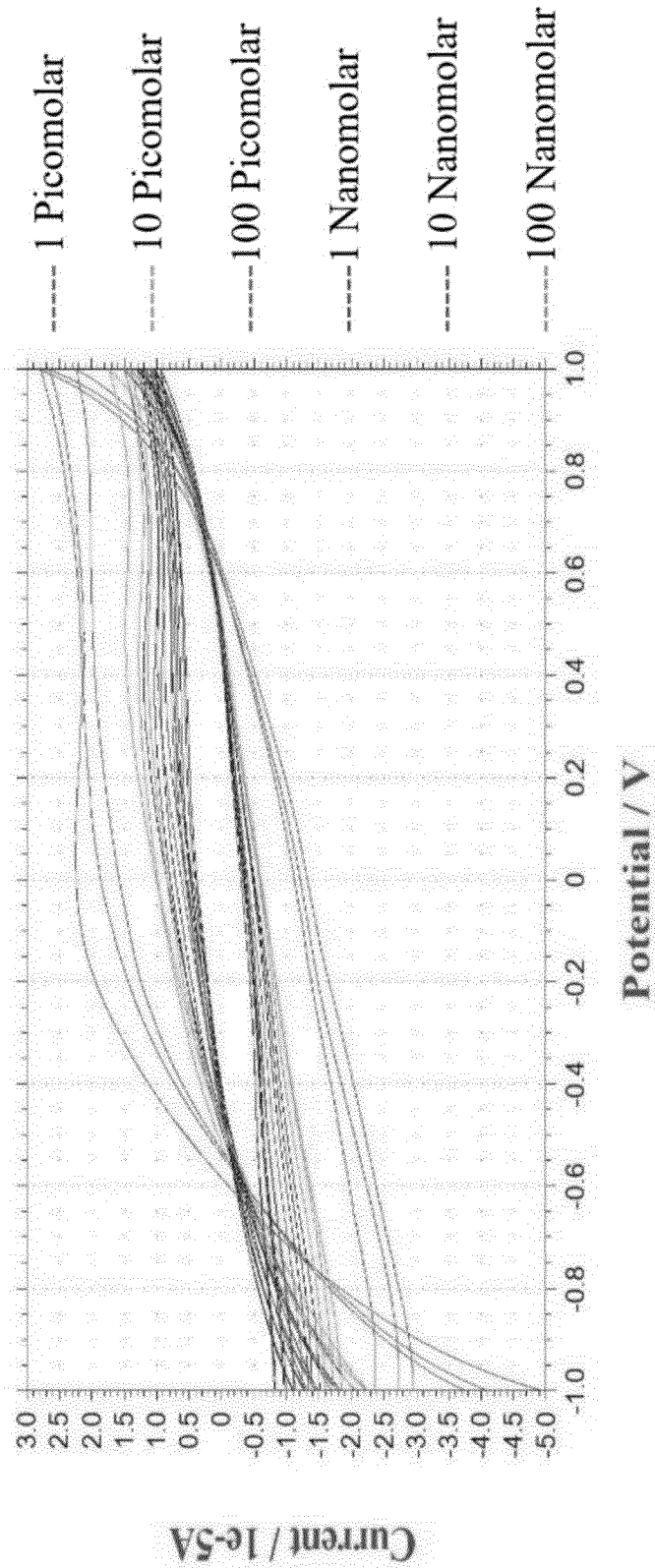
Figure 3:
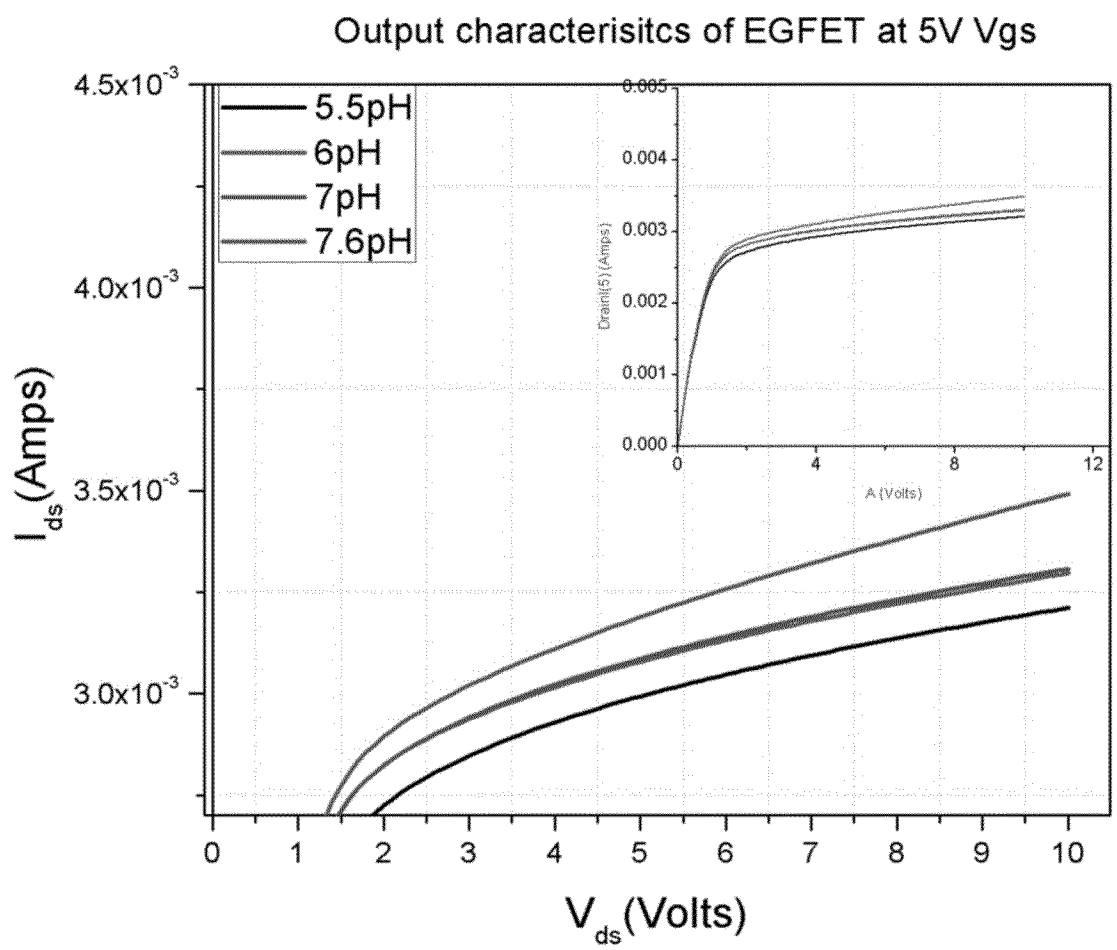
Figure 4:
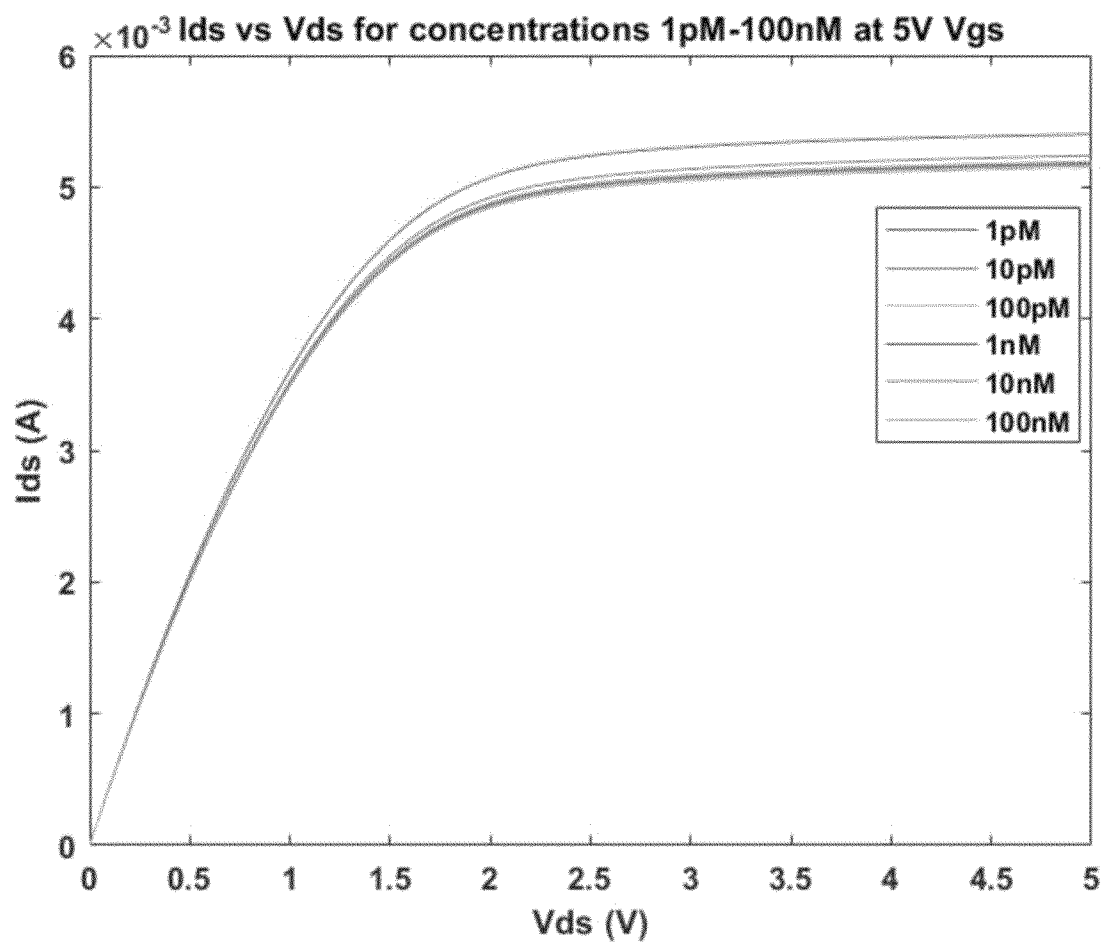
Figure 5:
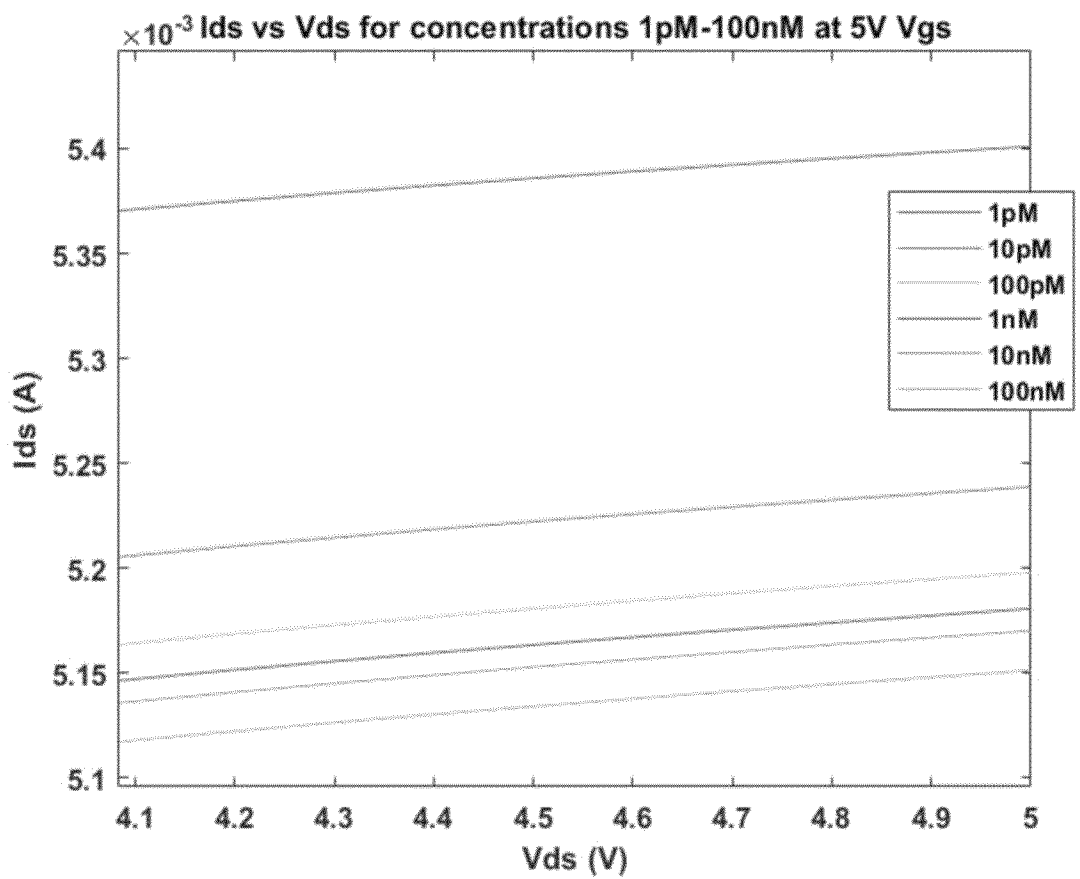
Figure 6:
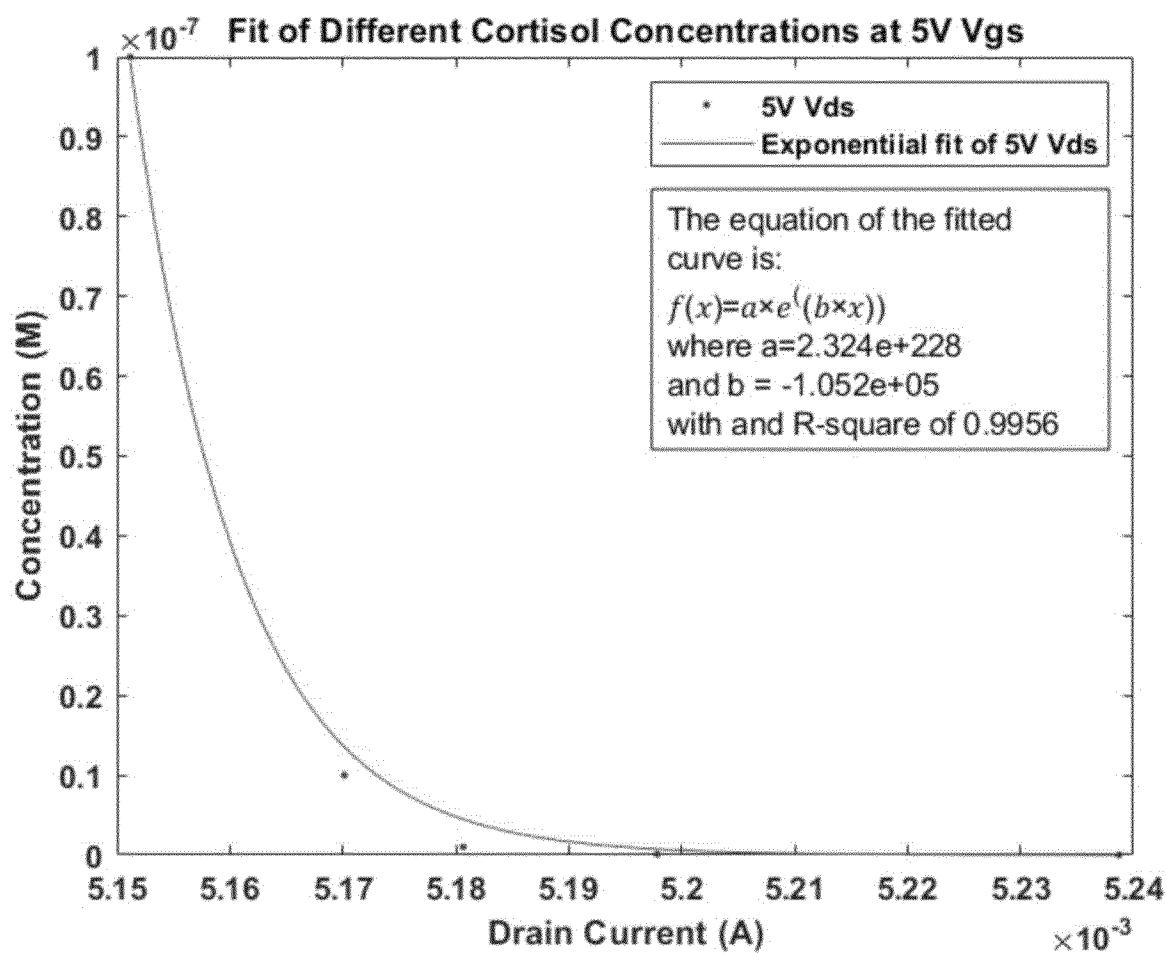
Figure 7:
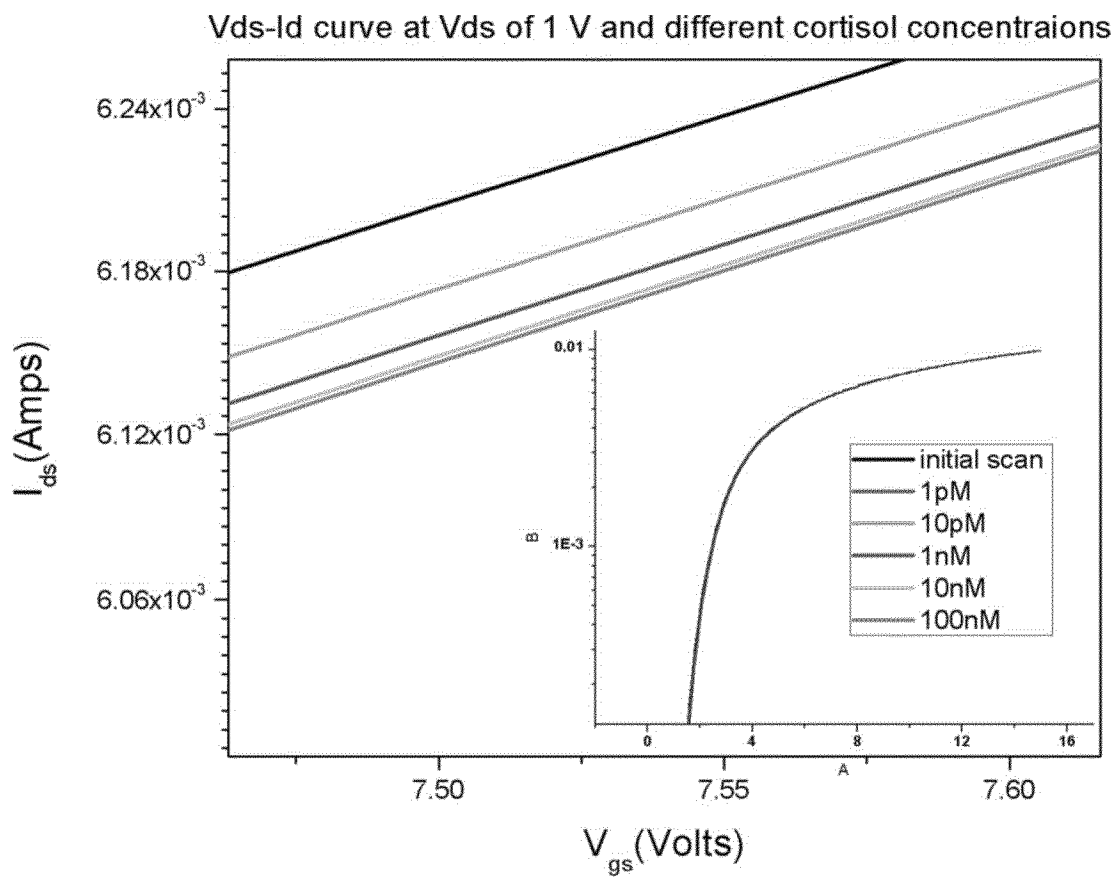
Figure 8:
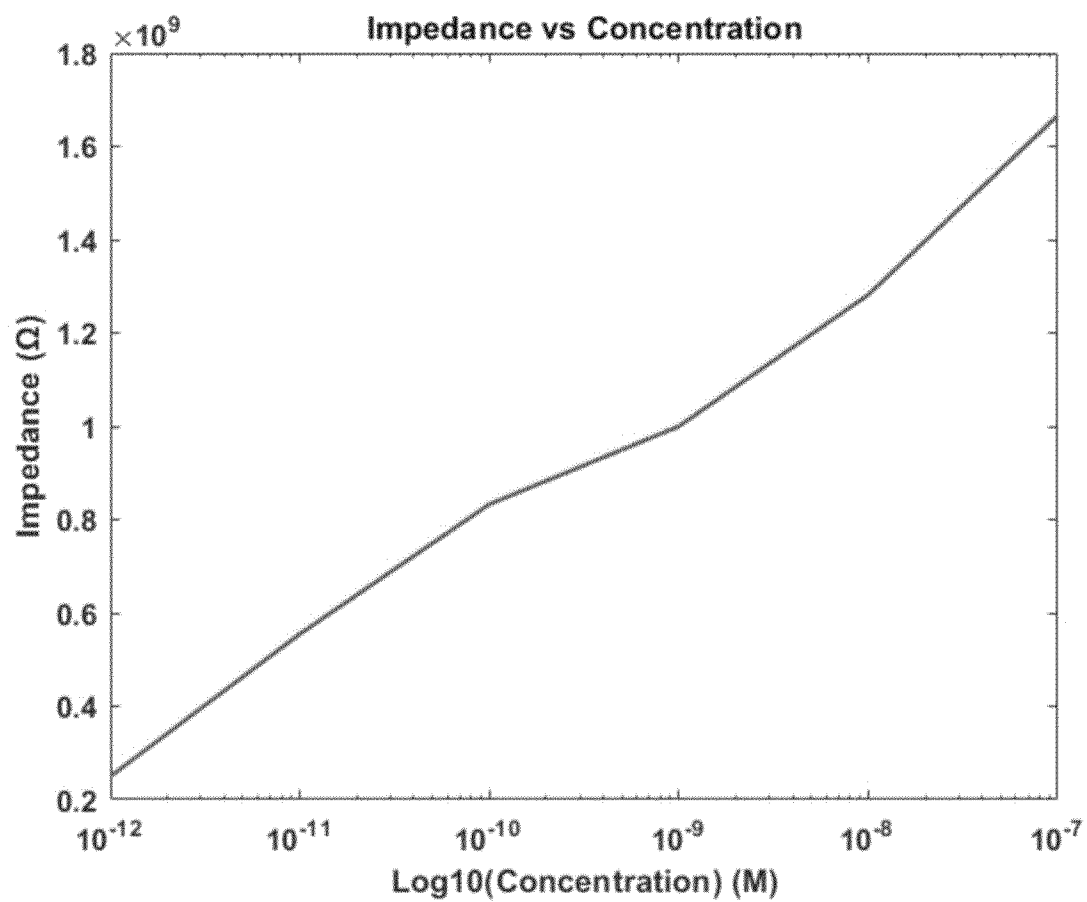
Figure 9:
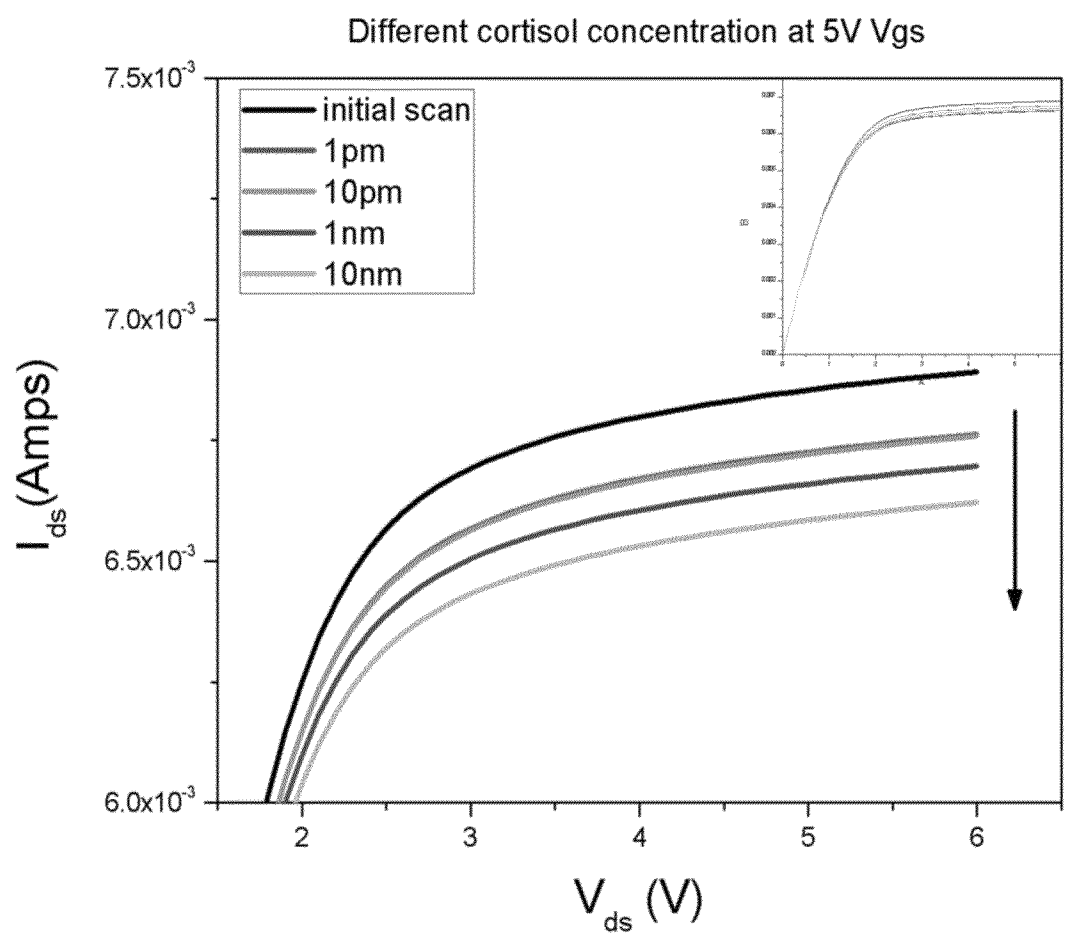
Figure 10:
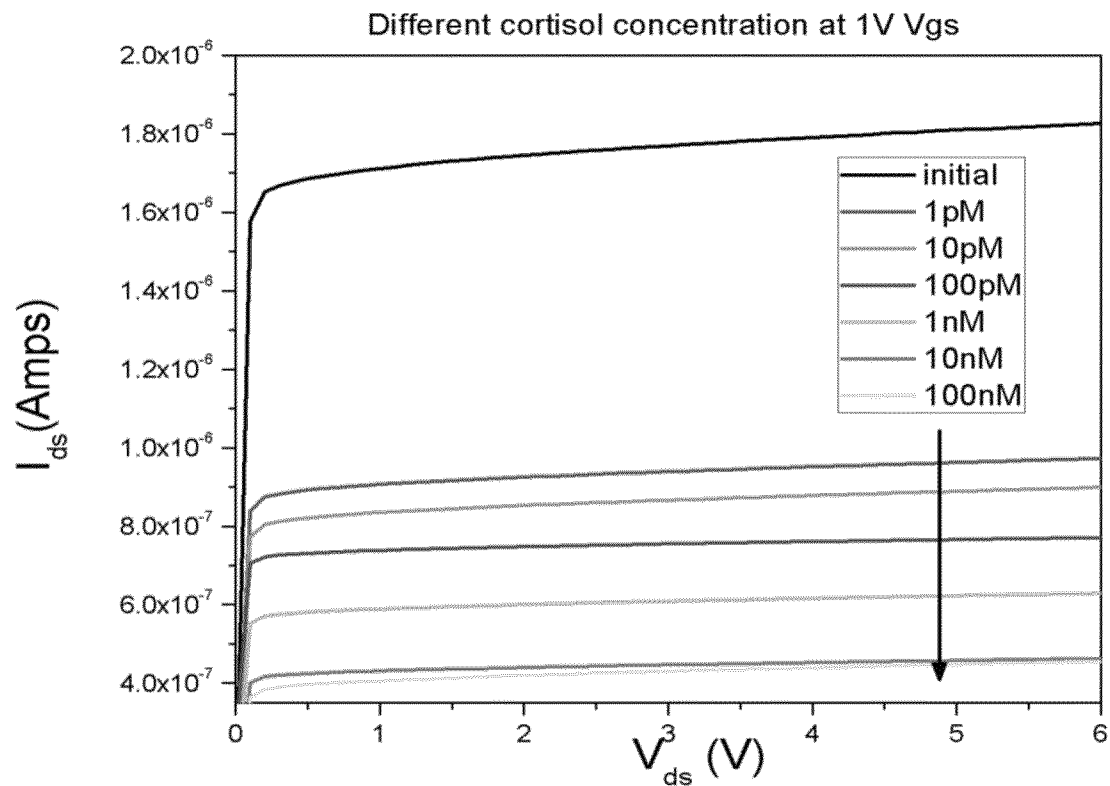
Figure 11:
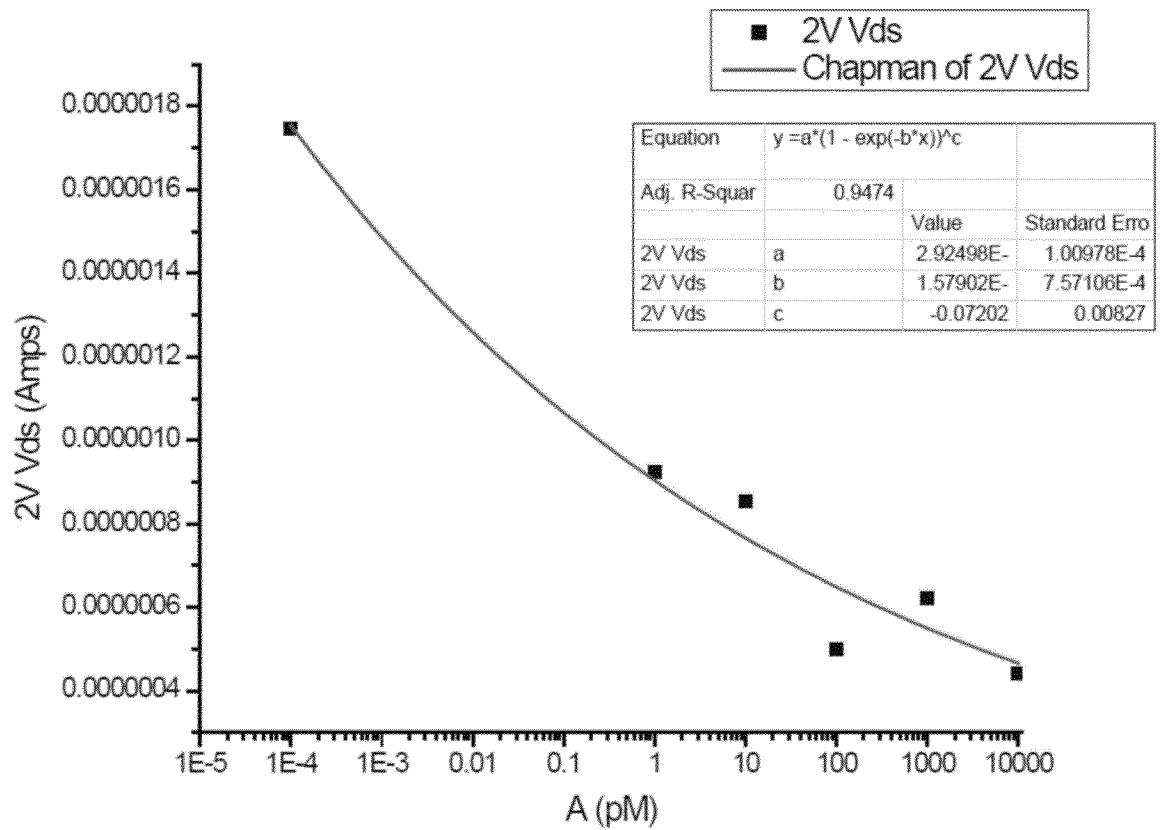
Figure 12:
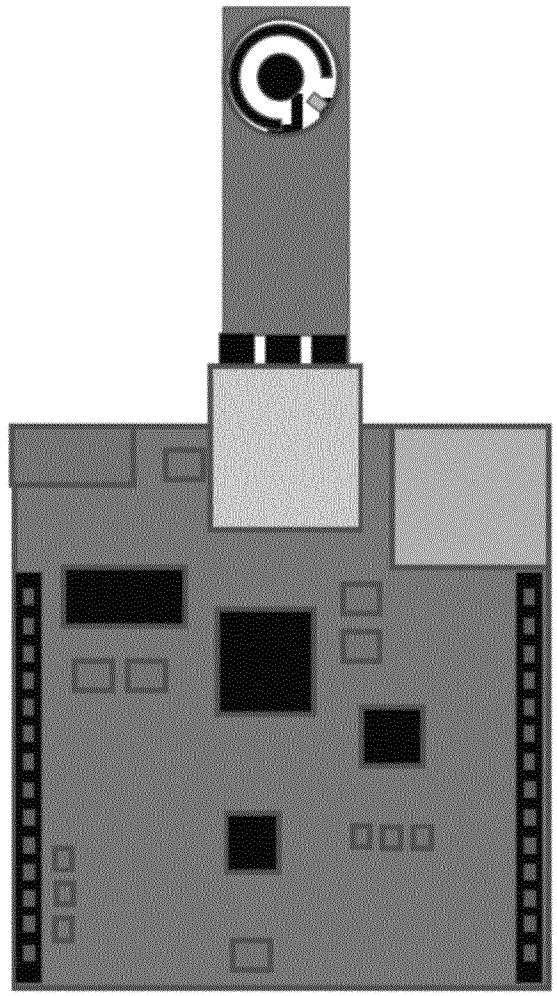
Figure 13:
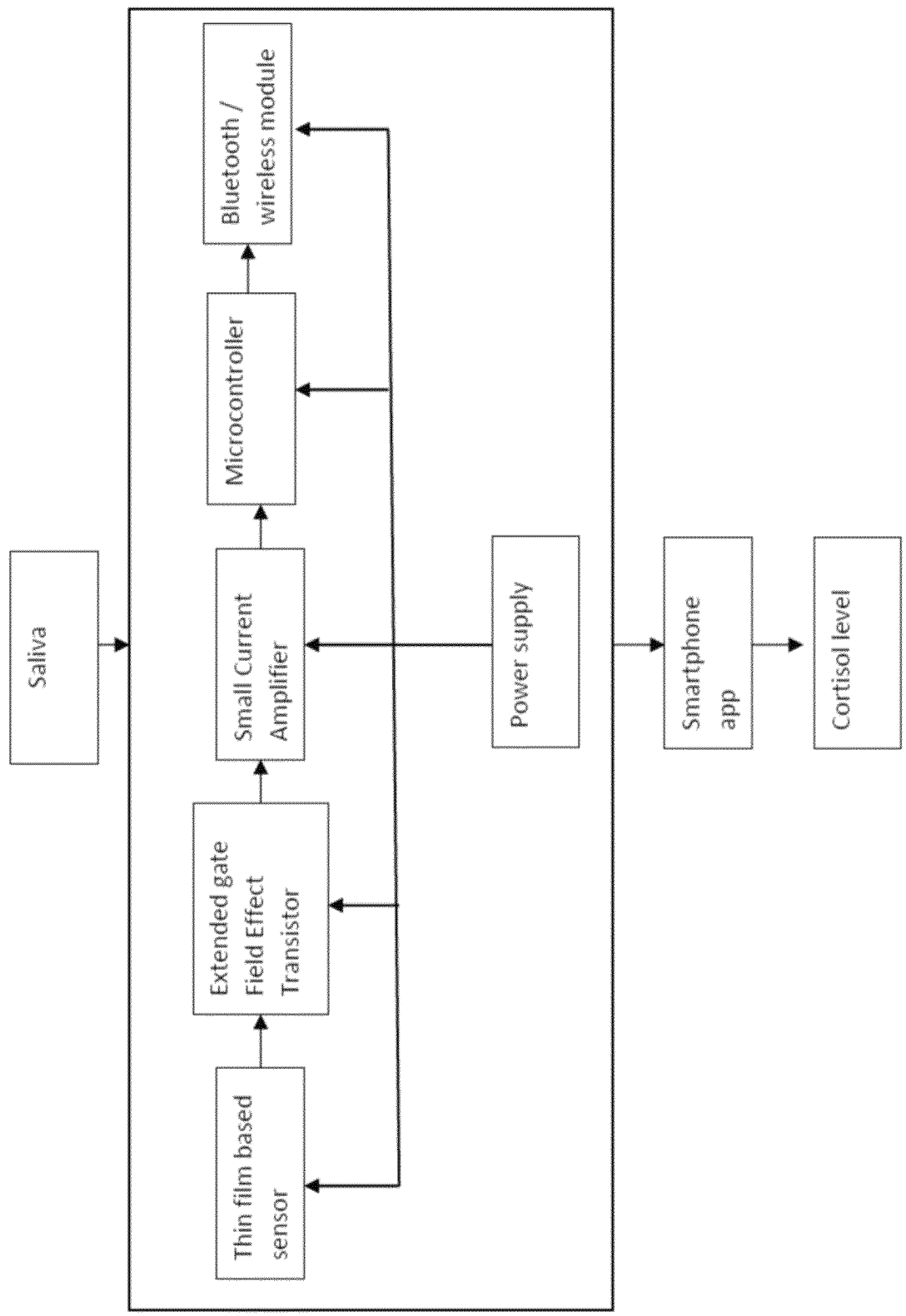

FIG. 13 shows a block diagram of a sensing system and method of the subject invention. Referring to FIG. 13, a fluid containing the analyte (e.g., saliva) can be provided to the sensing system (large box), which can include the thin-film-based sensor (e.g., MIP) and the EGFET. Optional elements of the sensing system include a small current amplifier, a microcontroller, and a Bluetooth/wireless module, any of which that are present can be in operable communication with the EGFET. Any or all of the elements of the sensing system can be powered by one or more power supply. The sensing system can optionally communicate with a mobile application (e.g., a smartphone app), which displays the analyte level (e.g., a cortisol level) to a user.

Embodiments of the subject invention can be used as portable sensing systems for the detection of biological and environmental targets/analytes. Embodiments provide a direct sensing output of the target species in the form of modulated source to drain current. The sensing layer is temperature stable, selective, sensitive, and cheaper to produce as compared to related art immunosensing methods. Sensing systems of embodiments are reusable and do not require any label or mediator for functioning, unlike related art electrochemical methods.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Example 1

A screen printed carbon electrode (SPCE) was used to fabricate an MIP with cortisol selectivity. The fabrication of MIP and stepwise characterization of MIP, along with details of cortisol sensing, have been discussed in Manickam et al. (supra), which is hereby incorporated herein by reference in its entirety. The MIP electrode, developed for cortisol sensing, was connected to the gate of the FET sensor, similar to what is shown in FIG. 1. The gate of the FET was connected to the working electrode of the SPCE. The gate voltage source was connected to the reference electrode of the SPCE. The source was grounded and the drain was connected to the power source. The output and transfer characteristics of the FET (CD4007UB) were measured using the Keithley 4200 source meter. The output and transfer characteristics were measured by connecting the gate directly to the $V_g$ power supply and varying the gate voltage. After establishing the baseline measurements of the transistor, measurements were made with 50 μL of phosphate-buffered saline (PBS) with different pH values. Subsequent measurements were made in PBS solution (7.6 pH) after incubating different cortisol concentrations on the MIP modified, extended gate.

Figure 2:
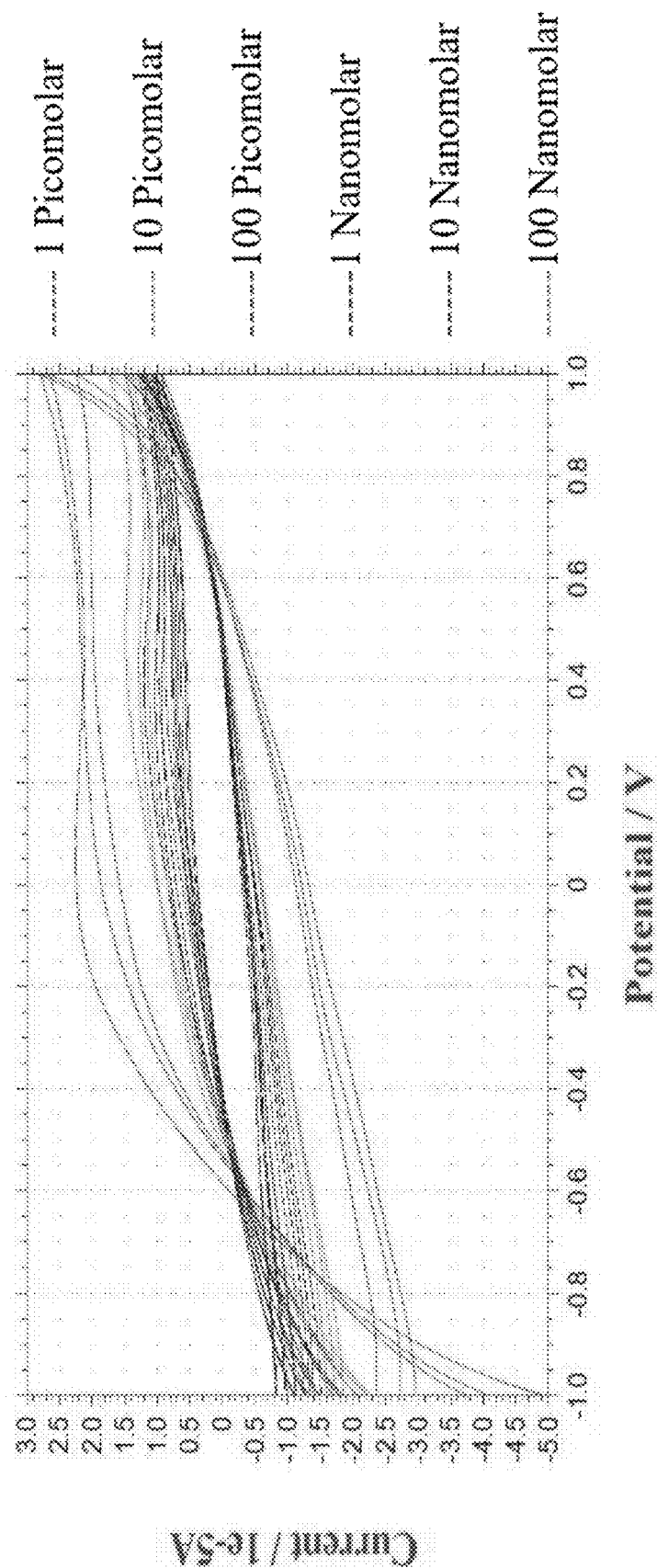
FIG. 2 shows a plot of current versus voltage at different pH values of a phosphate-buffered saline (PBS) solution.

The system was first tested without the extended gate to compare the output and transfer characteristics. The MIP was then tested without the FET system to verify the accuracy and selectivity of the extended gate. The MIP modified, extended gate was then connected to the FET and output characteristics were repeated with different pH solutions of PBS. Results are shown in FIG. 2, which shows current versus voltage curves of the MIP extended gates at different concentrations of PBS.

Figure 3:
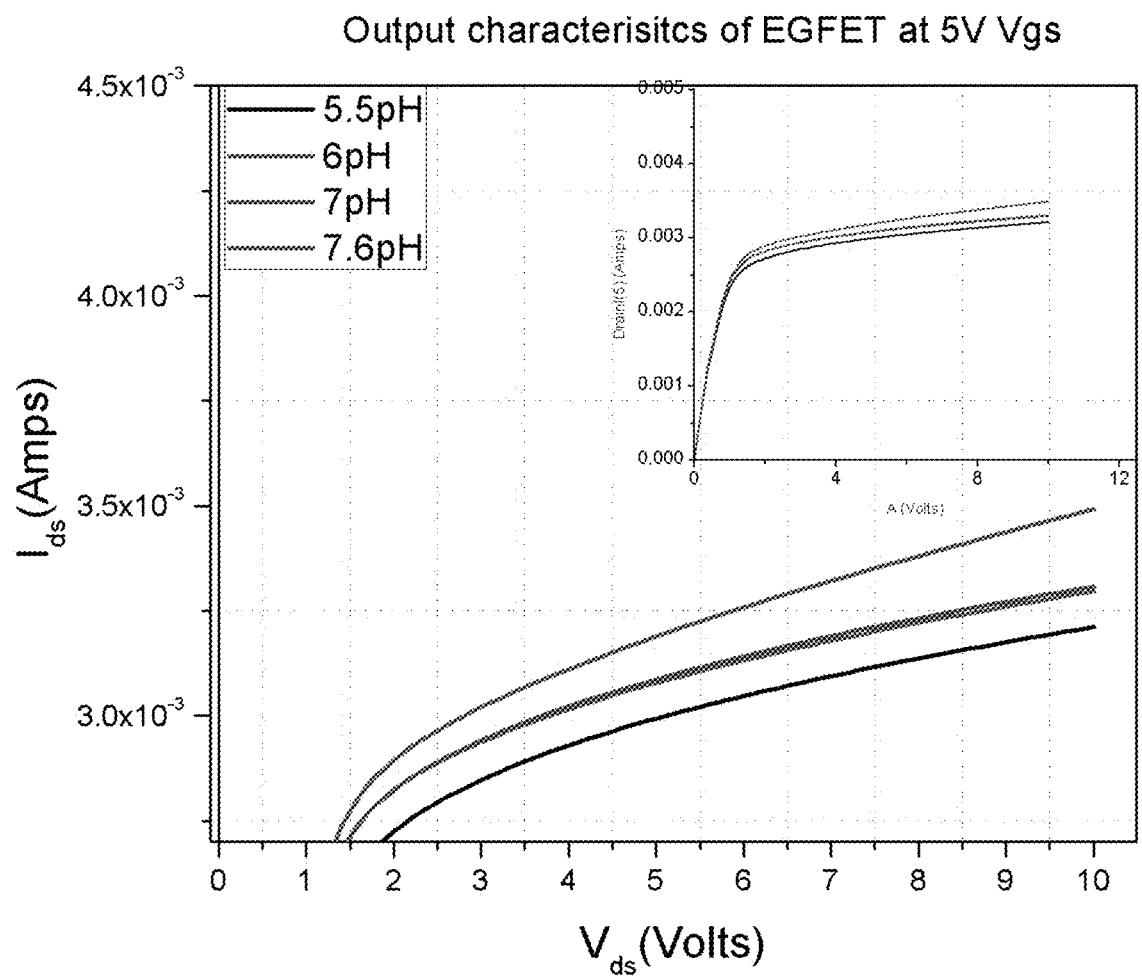
FIG. 3 shows the current response (drain-source current versus drain-source voltage) of an extended gate field effect transistor (EGFET) after the addition of PBS at different pH values, with a constant gate voltage of 5 volts (V).

To evaluate the MIP EGFET sensor, it was tested with a series of PBS solutions with four different pH values. The gate voltage was kept constant at 5 V. FIG. 3 shows the current response (drain-source current versus drain-source voltage) of the EGFET after the addition of PBS at different pH values, with the constant gate voltage of 5 V. The response of the system indicates that the current drops as the pH value changes from more neutral to more acidic (e.g., pH of 5.5.), indicating the formation of an ionic double layer. With lower pH values, the number of H+ ions in the solution is higher. This causes a stronger charge interaction at the surface of the MIP. This interaction results in a lower gate voltage and therefore a lower drain current. The highest response was obtained when a PBS solution of pH 7.6 was used. This value is closer to the pH of a biological system. Subsequent experiments were performed using the same pH (7.6).

Figure 4:
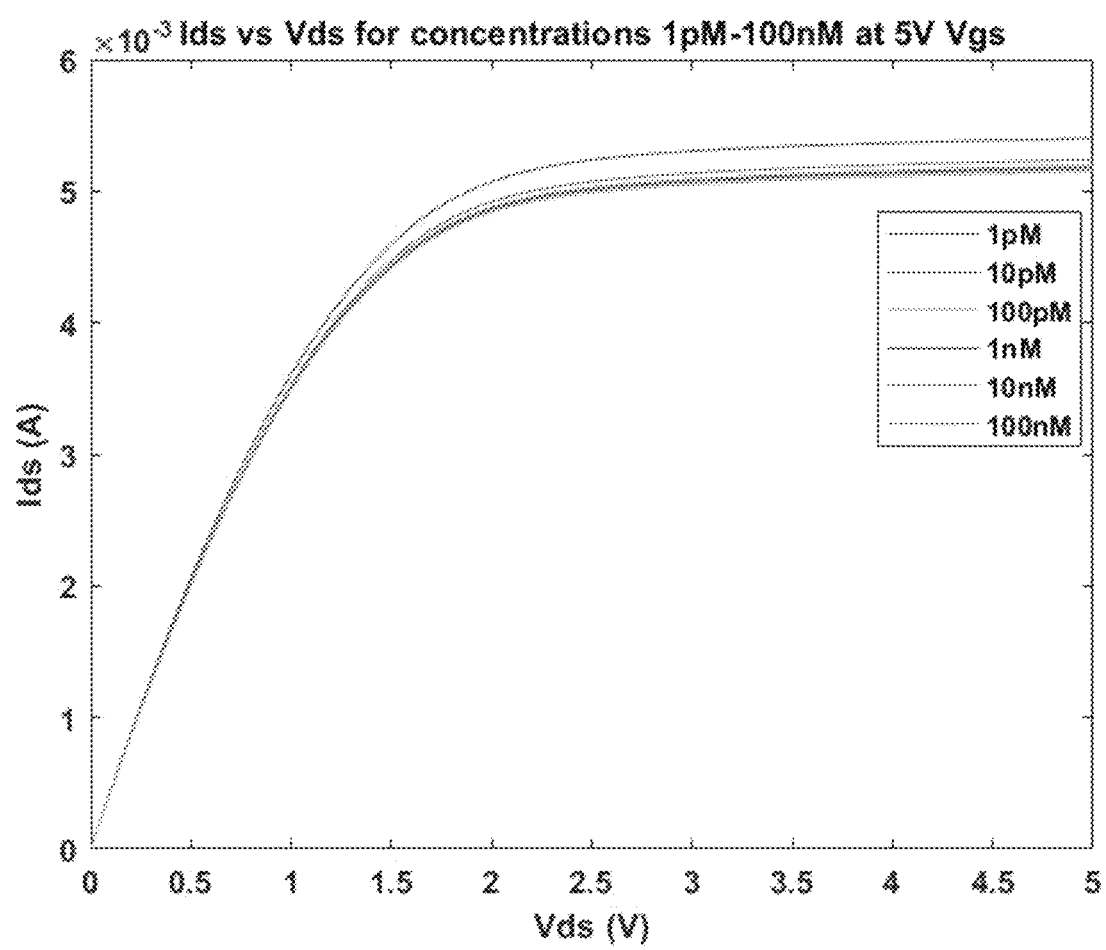
FIG. 4 shows output characteristics of different cortisol concentrations immobilized on an extended gate.
Figure 5:
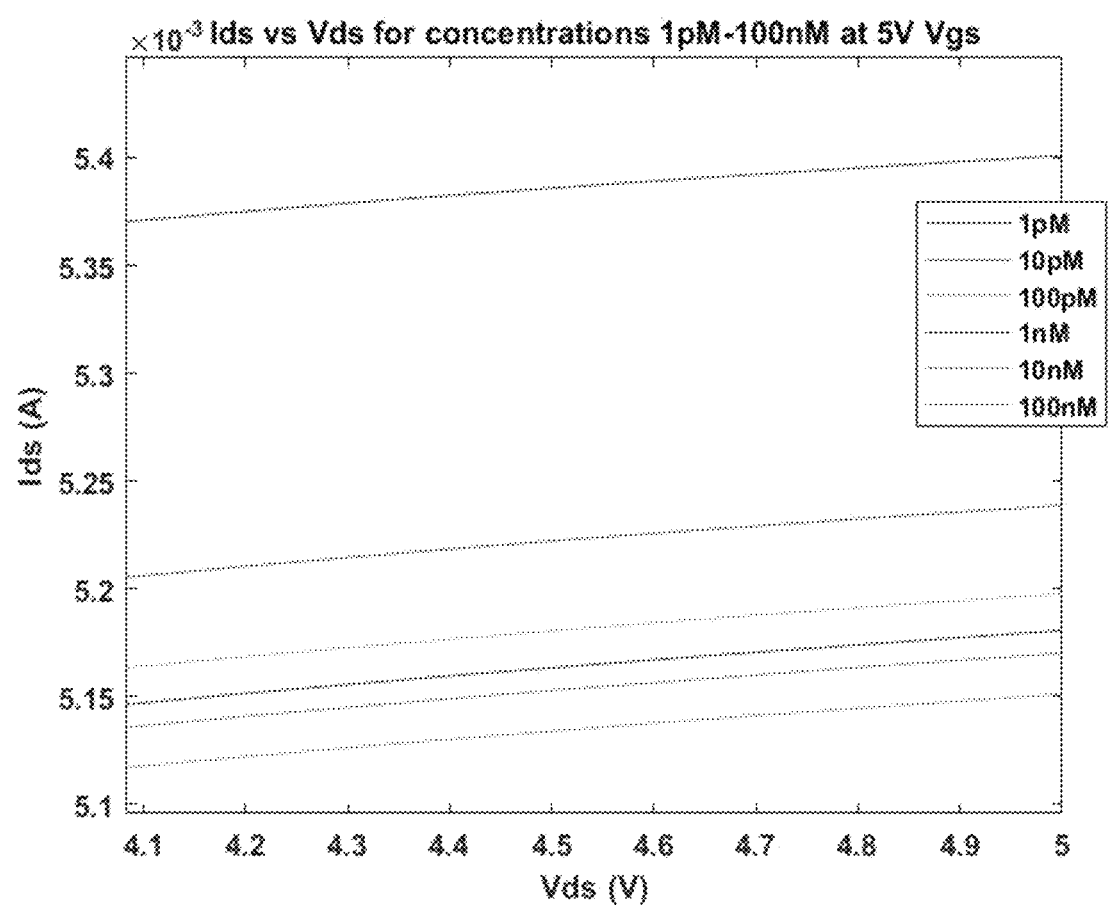
FIG. 5 shows output characteristics of different cortisol concentrations immobilized on an extended gate.

Cortisol stock solution was prepared by dissolving lyophilized cortisol powder in deionized water. The stock solution was then diluted to obtain different cortisol concentrations. The MIP modified electrode was incubated with 10 microliter (uL) of cortisol for 30 minutes. It was then washed away with DI water and dried with nitrogen. 50 uL of PBS was then dispensed on the electrode, and the current-voltage (I-V) measurements were made. FIGS. 4 and 5 show the output characteristics of different cortisol concentrations immobilized on the MIP modified, extended gate. The drain-source voltage ($V_{ds}$) was swept while the gate voltage was kept at 5 volts.

The reduction in drain current with increasing cortisol may be due to cortisol molecules occupying empty sites in the MIP matrix and reducing electron transport in the polymer matrix. The reduced gate current causes a reduction in the accumulated charges at the actual gate, thereby causing a decrease in source-drain current due to the reduced gate voltage.

Figure 6:
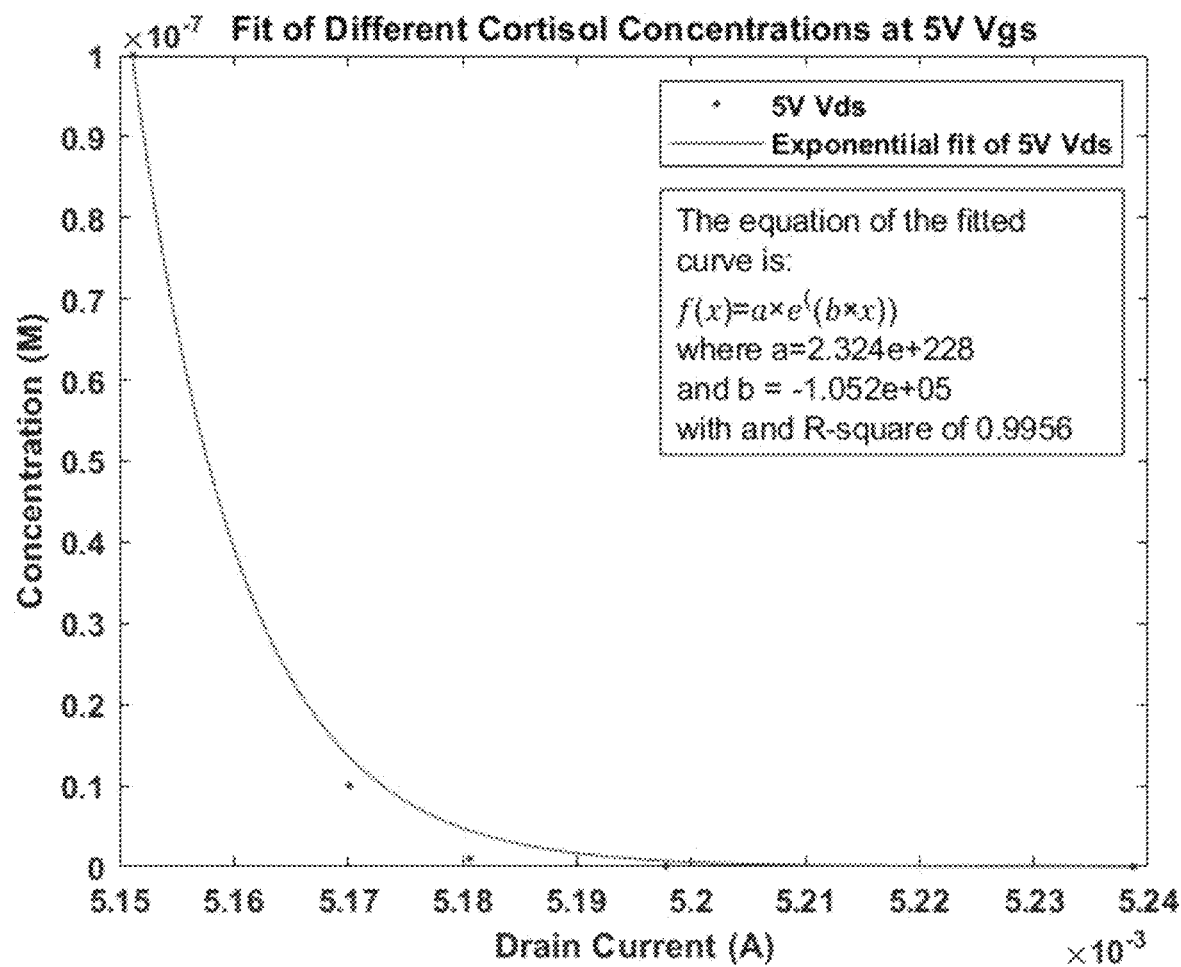
FIG. 6 shows a concentration curve of an EGFET device from 1 picomolar (pM) to 100 nanomolar (nM) cortisol concentration versus the current measured at a $V_{ds}$ of 5 V and a $V_{gs}$ of 5 V.

FIG. 6 shows the concentration curve of the EGFET device from 1 picomolar (pM) to 100 nanomolar (nM) cortisol concentration versus the current measured at a $V_{ds}$ of 5 V and a $V_{gs}$ of 5 V. This figure shows the concentration curve for cortisol as plotted from the $V_d$ versus $I_d$ data obtained in FIGS. 4 and 5. Drain current values at 5 volts were chosen and plotted against their respective concentration. The resulting exponential fit line is represented by the equation $(x) = a \times e^{((b \times x))}$, where $a = 2.324 \times 10^{228}$, and $b = -1.052 \times 10^5$ with an R-square value of 0.9956.

Figure 7:
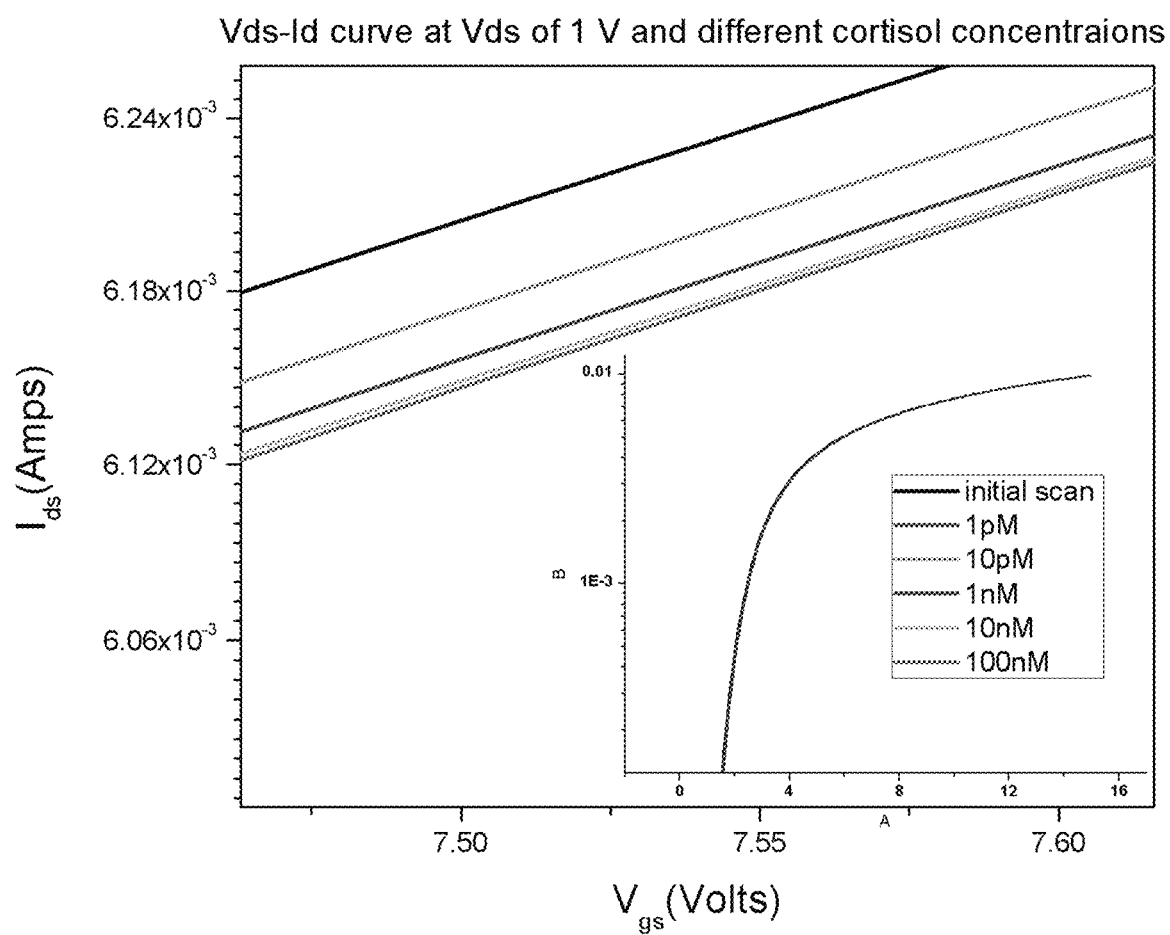
FIG. 7 shows a plot of drain-source current versus gate voltage of an EGFET device at different cortisol concentrations.
Figure 8:
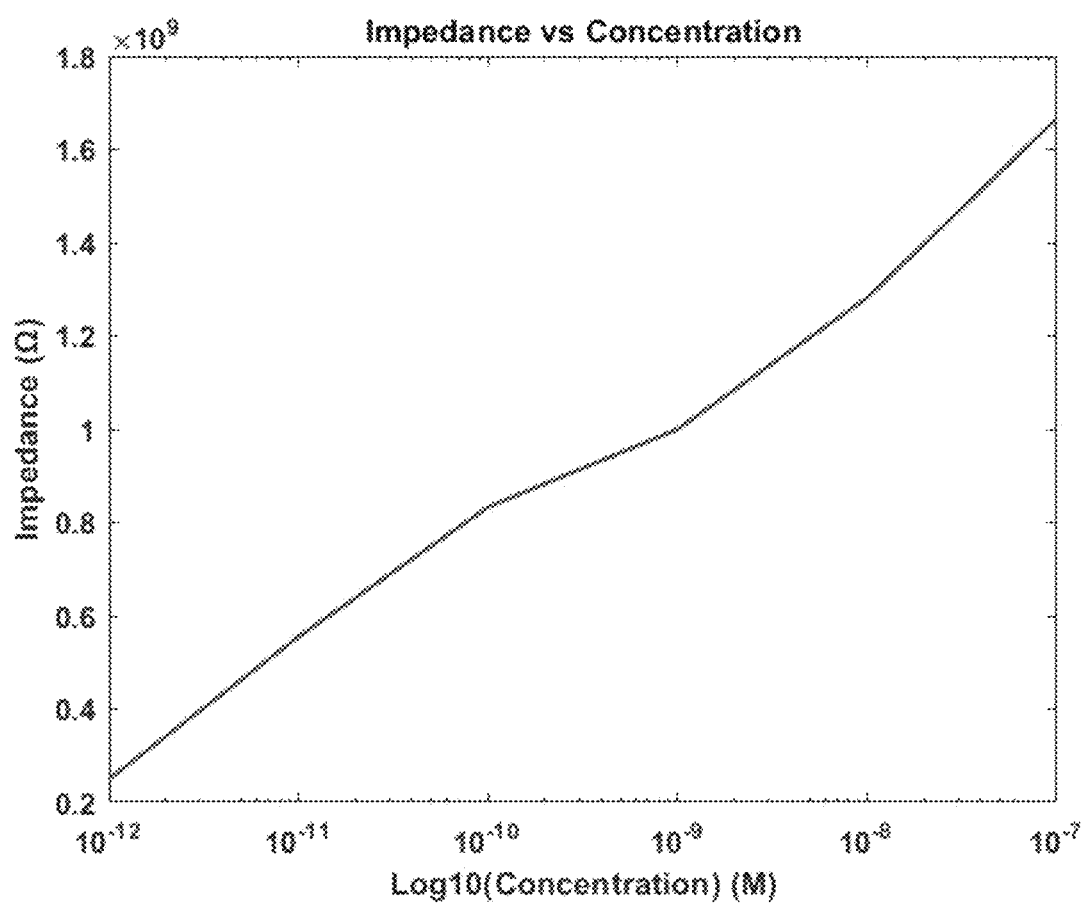
FIG. 8 shows a plot of effective impedance versus cortisol concentration (molar) on a logarithmic scale.

FIG. 7 shows a plot of drain-source current versus gate voltage of the EGFET-MIP device at different cortisol concentrations. The drain voltage was kept as 1V. FIG. 8 shows a plot of the effective impedance versus the cortisol concentration (molar) on a logarithmic scale. FIGS. 5 and 6 show a decrease in drain current can be observed as cortisol concentration increases, and FIG. 8 shows that an increase in the impedance of the MIP extended gate can be observed at the same time. The cortisol molecules occupy the empty sites in the polymer matrix, and the occupation of conductive sites by cortisol causes a change in the interaction of charge carriers with the polymer surface. The change in surface charges restricts the flow of current across the MIP thin film via an increase in impedance. The reduced current, in effect, decreases the electron density in the gate region of the n-type MOSFET working in enhancement mode. This change in drain current due to increased cortisol concentration is used for sensing purposes.

The results show that systems and methods of embodiments of the subject invention can be used POC sensing of cortisol (a vital steroid biomarker for detection of stress). Not only is the MIP-EGFET sensor much faster than alternatives (<1 minute), but it is also simple to use, label free, and provides a direct readout. The molecularly imprinted technique is a promising technique for bio-sensing application, and the selectivity of the MIP can be improved by computationally exploring the interaction between the polymer and the bio-analyte. Also, simulation studies of different binding sites at the polymer can be useful for better understanding of loading/elution mechanisms of the target molecule/analyte (e.g., computationally exploring the energy required for effective removal of the target molecule without affecting the molecular backbone). At the device end, the EGFET configuration can be incorporated with miniaturized electronics to provide a direct readout in handheld or wearable device form and integrated with MIP based sensing electrodes.

TABLE 1

MIP-EGFET sensor compared to common sensing systems

|  | SAM-based Sensing | MIP based sensing | MIP-EGFET sensor |
|---|---|---|---|
| Sensing Element | Monoclonal Antibodies | MIP | MIP |
| Detection Mode | CV | CV | EGFET |
| Label-free | No | Yes | Yes |
| Reusable | No | Yes | Yes |
| Selectivity | Yes | Yes | Yes |
| Limit of detection | 10 pg/mL | 0.0004 pg/mL | 0.0004 pg/mL |
| Direct readout | No | No | Yes |

The polypyrrole-based selective and validated MIP cortisol sensing chip was configured with an FET as an extended gate. The developed sensor was characterized and various concentrations of cortisol were detected using optimized pH and gate voltage. The device detected cortisol concentrations ranging from 1 pM to 100 nM and exhibited a detection range of 1 pM. Such a sensor provides label-free, fast, low-cost and direct sensing of cortisol. Due to the involvement of simple electronics and easy fabrication, a miniaturized cortisol sensing device can be used for POC applications.

Example 2

A screen printed carbon electrode (SPCE) was used to fabricate an MIP with cortisol selectivity, as with Example 1. The SPCE was a three-electrode system with an Ag/AgCl reference and two carbon electrodes. The thiol based crosslinker DTSP, and NaBH$_4$ were purchased from Thermo Fisher Scientific. Copper (II) Chloride (CuCl$_2$), KCl, and NaOH were obtained from Sigma Aldrich and used for deposition of copper nanoparticles. The buffer solution used for characterization was prepared from NaH$_2$PO$_4$ and Na$_2$HPO$_4$. These chemicals were also purchased from Sigma Aldrich. All the chemicals were of analytical grade and were used without further purification. The SPCE was combined with a commercially available FET for further experiments.

The MIP electrode was connected to the gate of the FET sensor, as shown in FIG. 1. The gate of the FET was connected to the working electrode of the SPCE. The gate voltage source was connected to the reference electrode of the SPCE. The source was grounded, and the drain was connected to the power source. The output and transfer characteristics of the FET were measured using the Keithley 4200 source meter. The output and transfer characteristics were measured by connecting the gate directly to the gate voltage ($V_g$) power supply and varying the gate voltage. After establishing the baseline measurements of the transistor, measurements were made with 50 μL of PBS with different pH values. Subsequent measurements were made in the PBS solution (7.6 pH) after incubating different cortisol concentrations on the MIP-modified, extended gate. The results were the same as those shown in FIG. 3.

Figure 9:
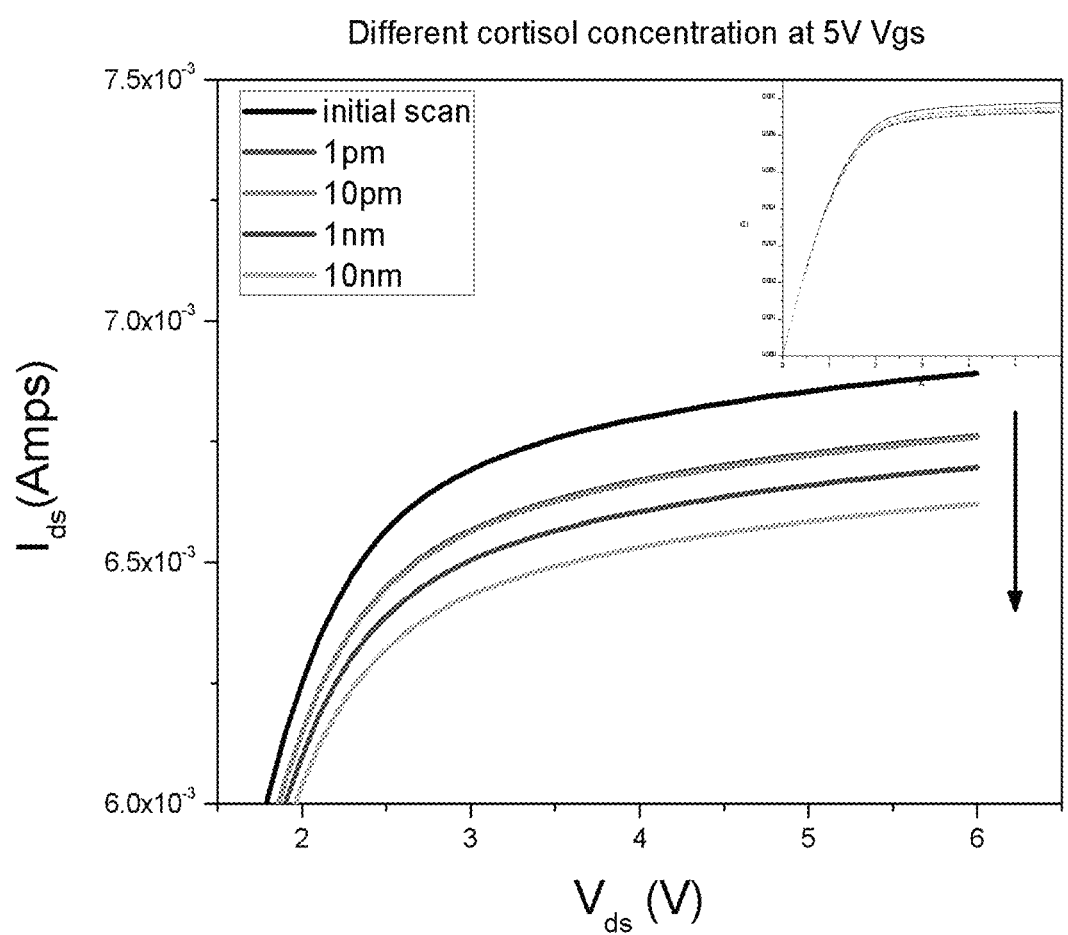
FIG. 9 shows output characteristics of different cortisol concentrations immobilized on an extended gate; the drain-source voltage was swept while the gate voltage was kept at 5 V.
Figure 10:
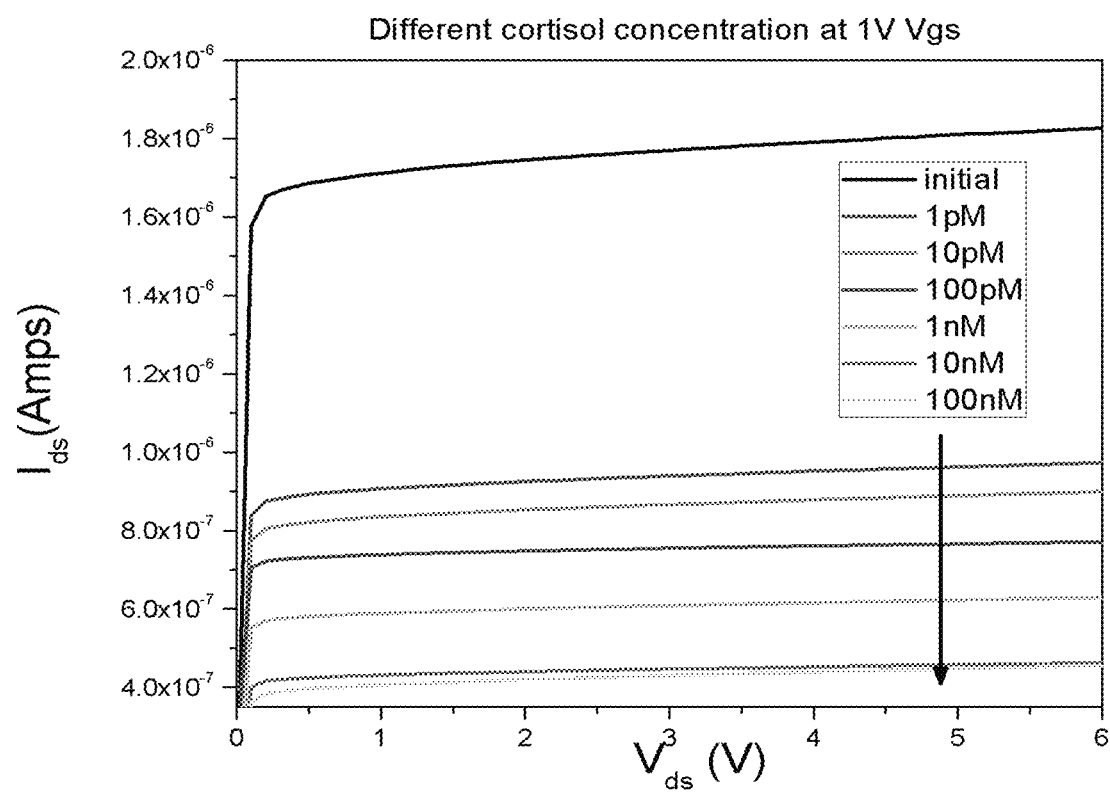
FIG. 10 shows output characteristics of different cortisol concentrations immobilized on an extended gate; the drain-source voltage was swept while the gate voltage was kept at 1 V.

Cortisol stock solution was prepared by dissolving lyophilized cortisol powder in ethanol and the PBS solution of pH of about 7.4. The stock solution was then diluted to obtain different cortisol concentrations. The MIP modified electrode was incubated with 10 uL of cortisol for 30 minutes. It was then washed away with deionized water and dried with nitrogen. 50 uL of PBS was then dispensed on the electrode, and the current-voltage measurements were made. FIGS. 9 and 10 show the output characteristics of different cortisol concentrations immobilized on the MIP modified, extended gate. The drain-source voltage was swept while the gate voltage was kept at 5 V (FIG. 9) and 1 V (FIG. 10).

Figure 11:
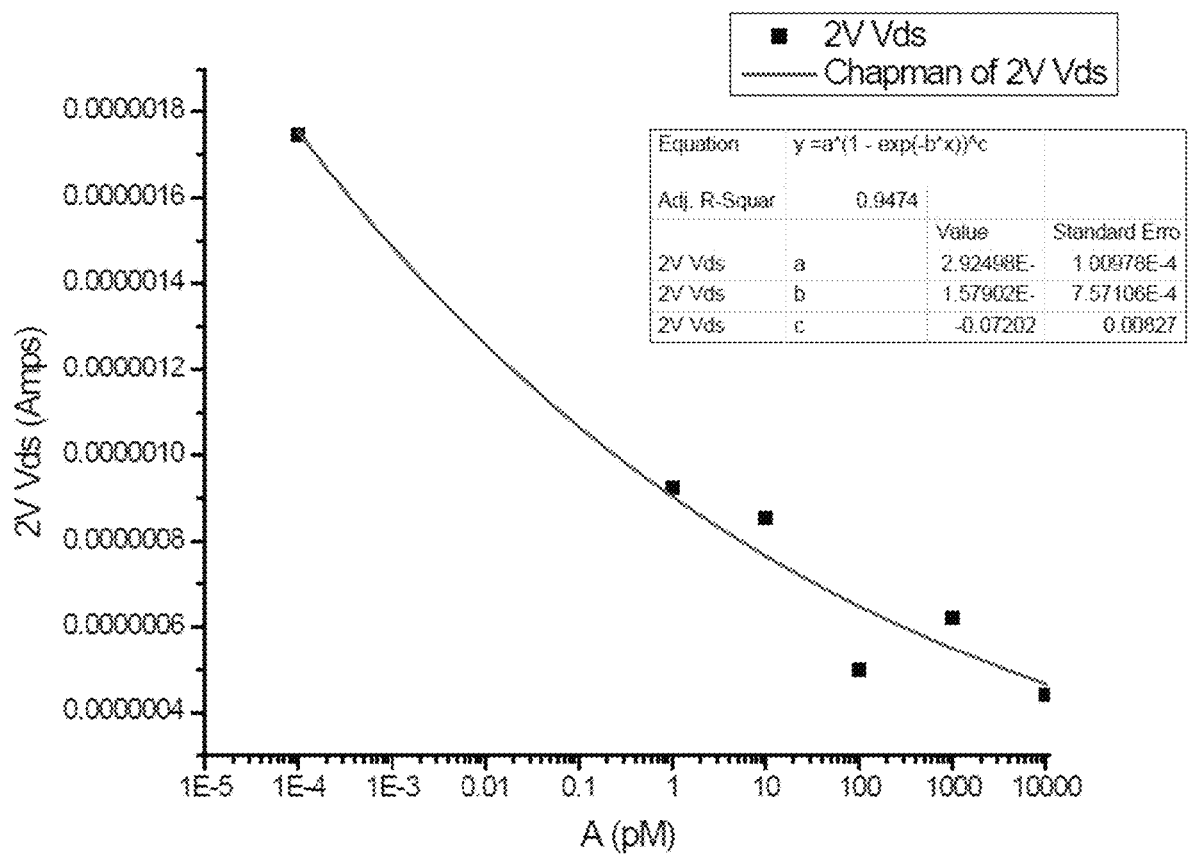
FIG. 11 shows the concentration curve for cortisol as plotted from the $I_d$ versus $V_d$ data obtained from FIG. 10.

FIG. 11 shows the concentration curve for cortisol as plotted from the $I_d$ versus $V_d$ data obtained in FIG. 10. Drain current values at 2 V were chosen and plotted against their respective concentration on a logarithmic scale.

As with Example 1, the device detected cortisol concentrations ranging from 1 pM to 100 nM and exhibited a detection range of 1 pM. Such a sensor provides label-free, fast, low-cost and direct sensing of cortisol. Due to the involvement of simple electronics and easy fabrication, a miniaturized cortisol sensing device can be used for POC applications.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A biosensing system for detecting a target biological analyte, the system comprising:
    a field effect transistor (FET) comprising a gate, a source, and a drain;
    an extended gate comprising a conductive substrate in electrical contact with the gate of the FET; and
    an external electrode that is not attached to the FET or the extended gate, configured to apply a gate voltage to a fluid disposed on a predefined area of the conductive substrate,
    the conductive substrate comprising a screen printed carbon electrode (SPCE) comprising a reference electrode and a working electrode,
    the extended gate being a single, continuous extended gate, and
    the reference electrode and the working electrode both being disposed on a same surface of the single continuous extended gate.

2. The biosensing system according to claim 1, the conductive substrate being a molecular imprinted polymer (MIP) that is specifically functionalized for the target biological analyte.

3. The biosensing system according to claim 1, the target biological analyte being cortisol.

4. The biosensing system according to claim 1, the external electrode being connected to a gate voltage source, the gate voltage source being connected to the reference electrode of the SPCE, and
    the gate of the FET being connected to the working electrode of the SPCE.

5. The biosensing system according to claim 1, the gate of the FET being connected to the working electrode of the SPCE.

6. The biosensing system according to claim 1, the drain of the FET being connected to a drain voltage source, and the source of the FET being grounded.

7. The biosensing system according to claim 1, the source of the FET being connected to a source voltage source, and the drain of the FET being grounded.

8. The biosensing system according to claim 1, the predefined area of the conductive substrate comprising a well in the conductive substrate configured to receive the fluid.

9. The biosensing system according to claim 1, further comprising:
    a small current amplifier in operable communication with the FET; and
    a microcontroller in operable communication with the small current amplifier,
    the microcontroller being configured to receive a source-drain characteristic and determine a concentration of the target biological analyte based on the source-drain characteristic, and
    the source-drain characteristic comprising at least one of a source-drain current and a source-drain voltage.

10. A method of sensing a concentration of a target biological analyte, the method comprising:
    providing a fluid comprising the target biological analyte to an extended gate comprising a single, continuous conductive substrate in electrical contact with the gate of a field effect transistor (FET), the FET comprising the gate, a source, and a drain;
    dipping an external electrode, which is not attached to the FET or the extended gate, in the fluid;
    providing a gate voltage to the external electrode via a gate voltage source connected to the external electrode;
    analyzing, by a controller in operable communication with the FET, a source-drain characteristic of the FET while the gate voltage is provided to the external electrode; and
    determining the concentration of the target biological molecule based on the source-drain characteristic of the FET,
    the source-drain characteristic comprising at least one of a source-drain current and a source-drain voltage,
    the conductive substrate comprising a screen printed carbon electrode (SPCE) comprising a reference electrode and a working electrode,
    the extended gate being a single, continuous extended gate, and
    the reference electrode and the working electrode both being disposed on a same surface of the single continuous extended gate.

11. The method according to claim 10, the conductive substrate being a molecular imprinted polymer (MIP) that is specifically functionalized for the target biological analyte.

12. The method according to claim 10, the target biological analyte being cortisol.

13. The method according to claim 10, the gate voltage source being connected to the reference electrode of the SPCE, and
    the gate of the FET being connected to the working electrode of the SPCE.

14. The method according to claim 10, the drain of the FET being connected to a drain voltage source, and the source of the FET being grounded.

15. The method according to claim 10, the source of the FET being connected to a source voltage source, and the drain of the FET being grounded.

16. The method according to claim 10, the fluid being provided to a predefined area of the conductive substrate, the predefined area comprising either: a) a well in the conductive substrate in which the fluid is deposited; or b) a flat area on an upper surface of the conductive substrate on which the fluid is deposited.

17. The method according to claim 10, in which a small current amplifier is in operable communication with the FET,
    the controller being a microcontroller in operable communication with the small current amplifier.

18. A method of sensing a concentration of a target biological analyte, the method comprising:

provided a fluid comprising the target biological analyte to an extended gate comprising a single, continuous conductive substrate in electrical contact with the gate of a field effect transistor (FET), the FET comprising the gate, a source, and a drain;

dipping an external electrode, which is not attached to the FET or the extended gate, in the fluid;

providing a gate voltage to the external electrode via a gate voltage source connected to the external electrode;

analyzing, by a controller in operable communication with the FET, a source-drain characteristic of the FET while the gate voltage is provided to the external electrode; and determining the concentration of the target biological molecule based on the source-drain characteristic of the FET, the source-drain characteristic comprising at least one of a source-drain current and a source-drain voltage, the conductive substrate being a molecular imprinted polymer (MIP) that is specifically functionalized for the target biological analyte, the target biological analyte being cortisol, the conductive substrate comprising a screen printed carbon electrode (SPCE) comprising a reference electrode and a working electrode, the gate voltage source being connected to the reference electrode of the SPCE, the gate of the FET being connected to the working electrode of the SPCE, the fluid being provided to a predefined area of the conductive substrate, the predefined area comprising either: a) a well in the conductive substrate in which the fluid is deposited; or b) a flat area on an upper surface of the conductive substrate on which the fluid is deposited, the controller being a microcontroller in operable communication with a small current amplifier that is in operable communication with the FET the extended gate being a single, continuous extended gate, and the reference electrode and the working electrode both being disposed on a same surface of the single, continuous extended gate.

* * * * *

UNITED STATES PATENT AND TRADEMARK OFFICE
CERTIFICATE OF CORRECTION

PATENT NO. : 10,739,305 B1
APPLICATION NO. : 16/669621
DATED : August 11, 2020
INVENTOR(S) : Shekhar Bhansali et al.

It is certified that error appears in the above-identified patent and that said Letters Patent is hereby corrected as shown below:

Please delete patent 10,739,305 B1 in its entirety and insert patent 10,739,305 B1 in its entirety.

Signed and Sealed this
Sixth Day of October, 2020

Andrei Iancu
*Director of the United States Patent and Trademark Office*

(12) United States Patent
Bhansali et al.

(10) Patent No.: US 10,739,305 B1
(45) Date of Patent: Aug. 11, 2020

(54) BIOSENSING SYSTEMS AND METHODS USING A FET

(71) Applicants: Shekhar Bhansali, Weston, FL (US); Syed Khalid Pasha, Miami, FL (US); Mubarak Ajmuddin Mujawar, Miami, FL (US)

(72) Inventors: Shekhar Bhansali, Weston, FL (US); Syed Khalid Pasha, Miami, FL (US); Mubarak Ajmuddin Mujawar, Miami, FL (US)

(73) Assignee: The Florida International University Board of Trustees, Miami, FL (US)

(*) Notice: Subject to any disclaimer, the term of this patent is extended or adjusted under 35 U.S.C. 154(b) by 0 days.

(21) Appl. No.: 16/669,621

(22) Filed: Oct. 31, 2019

(51) Int. Cl.
  *G01N 27/414* (2006.01)
(52) U.S. Cl.
  CPC .................. *G01N 27/4145* (2013.01)
(58) Field of Classification Search
  CPC .................................................. G01N 27/4145
  See application file for complete search history.

(56) References Cited

PUBLICATIONS

Parlak, Onur, et al. "Molecularly selective nanoporous membrane-based wearable organic electrochemical device for noninvasive cortisol sensing." Science advances 4.7 (2018).*
Maidin, Nur Nasyifa Mohd, et al. "Interaction of graphene electrolyte gate field-effect transistor for detection of cortisol biomarker." AIP Conference Proceedings. vol. 2045. No. 1. AIP Publishing LLC, 2018.*
Jang, Hyun-June, et al. "Electronic cortisol detection using an antibody-embedded polymer coupled to a field-effect transistor." ACS applied materials & interfaces 10.19 (2018): 16233-16237.*

* cited by examiner

*Primary Examiner* — Robert J Eom
(74) *Attorney, Agent, or Firm* — Saliwanchik, Lloyd & Eisenschenk

(57) ABSTRACT

Systems and methods for sensing analytes using an extended gate field effect transistor (EGFET) are provided. A biosensing system can utilize a biodetection layer on a substrate, which can be coupled to a field effect transistor (FET). The coupling can be such that the gate of the field effect transistor is connected to the substrate having the biodetection layer thereon. The functionalized substrate can include a well-defined area that can hold a specific, pre-determined volume of fluid on top of it. An external electrode can be dipped in the fluid and can then be connected to a power source supplying a gate voltage. The presence or concentration of the target analyte in the fluid can be determined based on the source-drain characteristics of the FET.

18 Claims, 13 Drawing Sheets

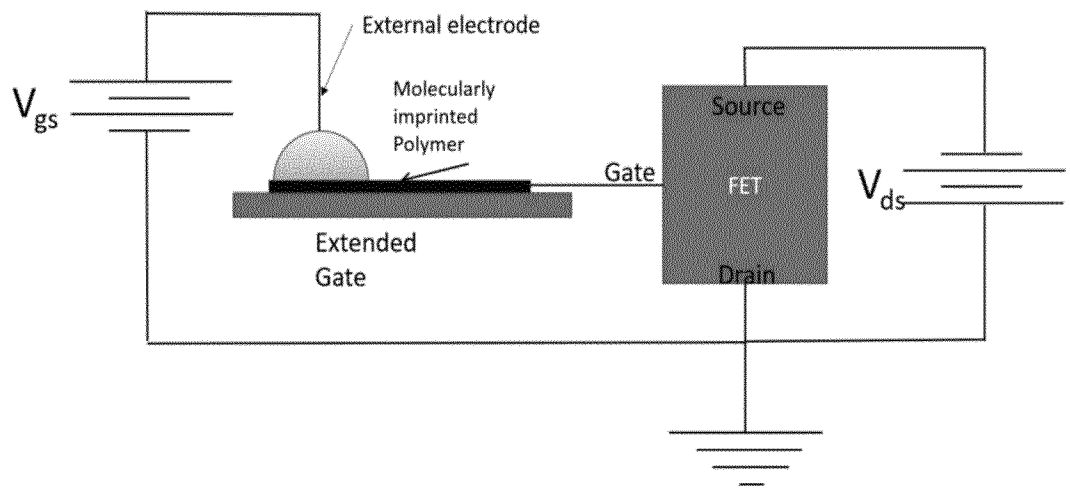

BIOSENSING SYSTEMS AND METHODS USING A FET

GOVERNMENT SUPPORT

This invention was made with government support under Award Number 1827682 awarded by the National Science Foundation (NSF). The government has certain rights in the invention.

BACKGROUND

Cortisol is produced in the adrenal glands and released into the blood stream of the body in response to stress. While everyone copes with stress differently, any high level of stress and overproduction of cortisol can lead to dangerous side effects including high blood pressure, severe fatigue, severe anxiety, and even depression. Excess production of cortisol is also linked to stress disorders, such as insomnia, Cushing's syndrome, and Post Traumatic Stress Disorder (PTSD). Depending on a person's pattern of activity, cortisol production may differ throughout the day. Typically, an individual who wakes up in the morning to work has the highest production of cortisol in the morning and lowest at night; this trend reverses if the individual has more rest in the morning and works late at night. Hence, continuous monitoring and point of care (POC) testing is the most optimal way to get the most accurate results for different patients.

As it stands now, patients must go out of their way and provide a sample to a clinic or laboratory. In addition, patients must wait a long time for samples to get processed and to receive result. This is detrimental because production levels of cortisol differ for each individual and sex throughout the day, meaning there can be inaccuracies in the results. POC testing is therefore important for personalized diagnosis and treatment.

Currently, a cortisol level from a sample can be detected using immunoassay chromatography, like enzyme-linked immunosorbent assay (ELISA). An electrochemical technique, cyclic voltammetry, is also used for characterization of cortisol in a sample. The systems used in these laboratories to detect the concentration of cortisol are bulky, expensive, time consuming, and require training to operate. As a result, patients don't have access to real-time, continuous monitoring or POC testing for cortisol. Similar problems exist in testing for many other analytes.

BRIEF SUMMARY

Embodiments of the subject invention provide advantageous systems and methods for sensing analytes (e.g., biological analytes) using an extended gate field effect transistor (EGFET). A biosensing system can utilize a biodetection layer (e.g., a synthetic biodetection layer) on a substrate (e.g., a conductive substrate), which can be coupled to a field effect transistor (FET). The method of coupling can be such that the gate of the field effect transistor is connected to the substrate having the synthetic biodetection layer thereon. The functionalized substrate can include a well-defined area (e.g., a well or a flat area) that can hold a specific, predetermined volume of fluid (e.g., liquid) on top of it. An external electrode can be dipped in the fluid and can then be connected to a power source supplying a voltage, which can be the gate voltage. The variations in the charge transfer from the external electrode to the gate electrode of the FET due to the presence of target molecules on the synthetic biodetection layer modulates the source to drain characteristics of the FET. These modulations can be then correlated to the concentration of the target analyte (e.g., based on an already known correlation due to a prior calibration or the like) that is present on the detection layer. Such a biosensing system offers many advantages, including a direct sensing output that can be correlated to the concentration of the target/analyte molecules in terms of the output current of the FET. In addition, this configuration allows for the isolation of the sensitive electronic components from the potentially corrosive environment of the fluids used for sensing (i.e., the FET components are isolated from the fluid containing the analyte).

In an embodiment, a biosensing system for detecting a target biological analyte can comprise: an FET comprising a gate, a source, and a drain; an extended gate comprising a conductive substrate in electrical contact with the gate of the FET; and an external electrode that is not attached to the FET or the extended gate, configured to apply a gate voltage to a fluid disposed on a predefined area of the conductive substrate. The conductive substrate can be an MIP that is specifically functionalized for the target biological analyte. The system can further comprise a screen printed carbon electrode (SPCE) disposed on the conductive substrate, the SPCE comprising a reference electrode and a working electrode. The external electrode can be connected to a gate voltage source, the gate voltage source can be connected to the reference electrode of the SPCE, and the gate of the FET can be connected to the working electrode of the SPCE. The drain of the FET can be connected to a drain voltage source with the source of the FET being grounded, or alternatively the source of the FET can be connected to a source voltage source with the drain of the FET being grounded. The predefined area of the conductive substrate can comprise a well in the conductive substrate configured to receive the fluid or a flat area on an upper surface of the conductive substrate designed to receive the fluid. The system can further comprise a small current amplifier in operable communication with the FET, and a microcontroller in operable communication with the small current amplifier; the microcontroller can be configured to receive a source-drain characteristic and determine a concentration of the target biological analyte based on the source-drain characteristic, and the source-drain characteristic can be a source-drain current, a source-drain voltage, or both.

In another embodiment, a method of sensing a concentration of a target biological analyte can comprise: providing a fluid comprising the target biological analyte to an extended gate comprising a conductive substrate in electrical contact with the gate of an FET, the FET comprising the gate, a source, and a drain; dipping an external electrode, which is not attached to the FET or the extended gate, in the fluid; providing a gate voltage to the external electrode via a gate voltage source connected to the external electrode; analyzing, by a controller in operable communication with the FET, a source-drain characteristic of the FET while the gate voltage is provided to the external electrode; and determining the concentration of the target biological molecule based on the source-drain characteristic of the FET. The source-drain characteristic can be a source-drain current, a source-drain voltage, or both.

BRIEF DESCRIPTION OF DRAWINGS

FIG. 1 shows a schematic view of a biosensing system according to an embodiment of the subject invention.

FIG. 2 shows a plot of current versus voltage at different pH values of a phosphate-buffered saline (PBS) solution.

FIG. 3 shows the current response (drain-source current versus drain-source voltage) of an extended gate field effect transistor (EGFET) after the addition of PBS at different pH values, with a constant gate voltage of 5 volts (V).

FIG. 4 shows output characteristics of different cortisol concentrations immobilized on an extended gate.

FIG. 5 shows output characteristics of different cortisol concentrations immobilized on an extended gate.

FIG. 6 shows a concentration curve of an EGFET device from 1 picomolar (pM) to 100 nanomolar (nM) cortisol concentration versus the current measured at a $V_{ds}$ of 5 V and a $V_{gs}$ of 5 V.

FIG. 7 shows a plot of drain-source current versus gate voltage of an EGFET device at different cortisol concentrations.

FIG. 8 shows a plot of effective impedance versus cortisol concentration (molar) on a logarithmic scale.

FIG. 9 shows output characteristics of different cortisol concentrations immobilized on an extended gate; the drain-source voltage was swept while the gate voltage was kept at 5 V.

FIG. 10 shows output characteristics of different cortisol concentrations immobilized on an extended gate; the drain-source voltage was swept while the gate voltage was kept at 1 V.

FIG. 11 shows the concentration curve for cortisol as plotted from the $I_d$ versus $V_d$ data obtained from FIG. 10.

FIG. 12 shows a top view of a biosensing system according to an embodiment of the subject invention.

FIG. 13 shows a block diagram view of a biosensing system/method according to an embodiment of the subject invention.

DETAILED DESCRIPTION

Embodiments of the subject invention provide advantageous systems and methods for sensing analytes (e.g., biological analytes) using an extended gate field effect transistor (EGFET). A biosensing system can utilize a biodetection layer (e.g., a synthetic biodetection layer) on a substrate (e.g., a conductive substrate), which can be coupled to a field effect transistor (FET). The method of coupling can be such that the gate of the field effect transistor is connected to the substrate having the synthetic biodetection layer thereon. The functionalized substrate can include a well-defined area (e.g., a well or a flat area) that can hold a specific, predetermined volume of fluid (e.g., liquid) on top of it. An external electrode can be dipped in the fluid and can then be connected to a power source supplying a voltage, which can be the gate voltage. The variations in the charge transfer from the external electrode to the gate electrode of the FET due to the presence of target molecules on the synthetic biodetection layer modulates the source to drain characteristics of the FET. These modulations can be then correlated to the concentration of the target analyte (e.g., based on an already known correlation due to a prior calibration or the like) that is present on the detection layer. Such a biosensing system offers many advantages, including a direct sensing output that can be correlated to the concentration of the target/analyte molecules in terms of the output current of the FET. In addition, this configuration allows for the isolation of the sensitive electronic components from the potentially corrosive environment of the fluids used for sensing (i.e., the FET components are isolated from the fluid containing the analyte).

In many embodiments, a molecular imprinted polymer (MIP) (e.g., a polypyrrole-based MIP) can be used as the biodetection layer, or as at least part of the biodetection layer. MIPs are discussed in detail in Manickam et al. (P. Manickam, S. K. Pasha, S. A. Snipes, and S. Bhansali, "A Reusable Electrochemical Biosensor for Monitoring of Small Molecules (Cortisol) Using Molecularly Imprinted Polymers," J. Electrochem. Soc., vol. 164, no. 2, pp. B54-B59, 2017), which is a prior work of the inventors and is hereby incorporated herein by reference in its entirety. The MIP can either be conductive and can be connected to the gate of the FET sensor, as shown in FIG. 1.

Electrochemical (EC)/electrical (e.g., FET, chemiresistive) sensors demonstrate good sensing performance (for a wide variety of analytes including but not limited to cortisol), can be made label-free, can be micro-fabricated, can provide fast results, and are suitable for miniaturization. Electrochemical sensing platforms (e.g., EC cortisol sensing platforms) can be integrated into a point of care (POC) system for continuous monitoring (e.g., online continuous monitoring) of cortisol as a function of one's environment. These systems are crucial for the detection of a targeted analyte outside controlled environments of diagnostic labs and hospitals and have a major impact on the applications of personal care, health, food, and environmental monitoring. An ideal POC biosensor device allows real-time, rapid, label-free, and multiplexed detection with high selectivity and sensitivity. Several challenges do exist in implementing POC sensors. The requirement of redox media for EC sensing adds to design complication for POC devices. The lack of robustness due to the temperature sensitivity of detection molecules (e.g., antibodies, enzymes) pose logistical challenges involving increased costs associated with storage at temperatures below 0° C. The complexity of the electronic system associated with these devices also inhibits or prevents them from being miniaturized for POC applications. Embodiments of the subject invention address these challenges.

A field effect transistor (FET) is active semiconductor device that modulates the flow of the drain current according to the applied charge on the gate electrode. Equation 1 below expresses the magnitude of drain current of a FET with respect to different parameters.

$$I_d = \beta\left(V_{gs} - V_T - \frac{1}{2}V_{ds}\right)V_{ds}I_d \quad (1)$$

where $V_T$ is the threshold voltage. The threshold voltage is the value of $V_{gs}$ beyond which the narrow conduction channel starts forming. $\beta$ is the trans-conductance parameter as expressed in Equation 2.

$$\beta = \mu C_{ox}\frac{W}{L} \quad (2)$$

$\beta$ is a function of the mobility of the electrons ($\mu$) in the inversion layer, the gate insulator capacitance per area ($C_{ox}$) and the channel width to length ratio (W/L).

The property of FETs in which drain currents being modulated due to the presence of charge on the gate surface can be utilized for electrophysiological applications resulting in a sensor. Immobilization of bio-functionalized moieties on the surface of the gate causes a change in the capacitance. This, in turn, modulates the drain current of the FET resulting in a configuration called an Ion Sensitive FET (ISFET). ISFETs can be used as biosensors due to fast response time, high sensitivity, batch processing, and the possibility of integrating on a single chip. However, this configuration can destroy the device due to the often harsh chemical nature of the electrolytes used. The open gate configuration also exposes the device to electromagnetic interference that can result in noisy data. Embodiments of the subject invention address these problems with ISFETs by using an extended gate.

Systems and method of embodiments of the subject invention circumvent the problems discussed in the previous paragraph by using an extended gate FET (EGFET) to isolate the chemical environment from the FET itself. Referring to FIG. 1, in an embodiment, a system can include an external functionalized substrate that is connected to the gate of the FET. The FET also includes a source and a drain, along with the insulator and gate electrode of the gate. The external electrode can touches the electrolyte, and a gate voltage is applied across the external electrode. The interaction between the ions present in the electrolyte and the functional group present on the extended gate substrate causes a surface potential change. This change of potential causes a change in the flow of current to the gate of the FET. In turn, the gate current modulates the drain-source current in the FET. The modulation of drain current due to the presence of biomolecules on the surface of the extended gate makes it possible to use the FET as a biosensor. This configuration allows for the stabilization of FET output by isolating it from changes happening due to pH, optical variations, and temperature variations because the gate material is not directly exposed to the environment or the chemicals. Although sensing of cortisol is discussed extensively herein, this is for exemplary purposes only and systems and method of embodiments of the subject invention can be used to sense any suitable analyte. FIG. 12 also shows a biosensing system according to an embodiment of the subject invention. Referring to FIG. 12, a top view is shown and integrated electronics (lower section of figure) can be seen as well, allowing for a portable format. The top portion of the figure shows the extended gate in contact with the FET.

FIG. 13 shows a block diagram of a sensing system and method of the subject invention. Referring to FIG. 13, a fluid containing the analyte (e.g., saliva) can be provided to the sensing system (large box), which can include the thin-film-based sensor (e.g., MIP) and the EGFET. Optional elements of the sensing system include a small current amplifier, a microcontroller, and a Bluetooth/wireless module, any of which that are present can be in operable communication with the EGFET. Any or all of the elements of the sensing system can be powered by one or more power supply. The sensing system can optionally communicate with a mobile application (e.g., a smartphone app), which displays the analyte level (e.g., a cortisol level) to a user.

Embodiments of the subject invention can be used as portable sensing systems for the detection of biological and environmental targets/analytes. Embodiments provide a direct sensing output of the target species in the form of modulated source to drain current. The sensing layer is temperature stable, selective, sensitive, and cheaper to produce as compared to related art immunosensing methods. Sensing systems of embodiments are reusable and do not require any label or mediator for functioning, unlike related art electrochemical methods.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to the invention.

Example 1

A screen printed carbon electrode (SPCE) was used to fabricate an MIP with cortisol selectivity. The fabrication of MIP and stepwise characterization of MIP, along with details of cortisol sensing, have been discussed in Manickam et al. (supra), which is hereby incorporated herein by reference in its entirety. The MIP electrode, developed for cortisol sensing, was connected to the gate of the FET sensor, similar to what is shown in FIG. 1. The gate of the FET was connected to the working electrode of the SPCE. The gate voltage source was connected to the reference electrode of the SPCE. The source was grounded and the drain was connected to the power source. The output and transfer characteristics of the FET (CD4007UB) were measured using the Keithley 4200 source meter. The output and transfer characteristics were measured by connecting the gate directly to the $V_g$ power supply and varying the gate voltage. After establishing the baseline measurements of the transistor, measurements were made with 50 µL of phosphate-buffered saline (PBS) with different pH values. Subsequent measurements were made in PBS solution (7.6 pH) after incubating different cortisol concentrations on the MIP modified, extended gate.

The system was first tested without the extended gate to compare the output and transfer characteristics. The MIP was then tested without the FET system to verify the accuracy and selectivity of the extended gate. The MIP modified, extended gate was then connected to the FET and output characteristics were repeated with different pH solutions of PBS. Results are shown in FIG. 2, which shows current versus voltage curves of the MIP extended gates at different concentrations of PBS.

To evaluate the MIP EGFET sensor, it was tested with a series of PBS solutions with four different pH values. The gate voltage was kept constant at 5 V. FIG. 3 shows the current response (drain-source current versus drain-source voltage) of the EGFET after the addition of PBS at different pH values, with the constant gate voltage of 5 V. The response of the system indicates that the current drops as the pH value changes from more neutral to more acidic (e.g., pH of 5.5.), indicating the formation of an ionic double layer. With lower pH values, the number of H+ ions in the solution is higher. This causes a stronger charge interaction at the surface of the MIP. This interaction results in a lower gate voltage and therefore a lower drain current. The highest response was obtained when a PBS solution of pH 7.6 was used. This value is closer to the pH of a biological system. Subsequent experiments were performed using the same pH (7.6).

Cortisol stock solution was prepared by dissolving lyophilized cortisol powder in deionized water. The stock solution was then diluted to obtain different cortisol concentrations. The MIP modified electrode was incubated with 10 microliter (uL) of cortisol for 30 minutes. It was then washed away with DI water and dried with nitrogen. 50 uL of PBS was then dispensed on the electrode, and the current-voltage (I-V) measurements were made. FIGS. 4 and 5 show the output characteristics of different cortisol concentrations immobilized on the MIP modified, extended gate. The drain-source voltage ($V_{ds}$) was swept while the gate voltage was kept at 5 volts.

The reduction in drain current with increasing cortisol may be due to cortisol molecules occupying empty sites in the MIP matrix and reducing electron transport in the polymer matrix. The reduced gate current causes a reduction in the accumulated charges at the actual gate, thereby causing a decrease in source-drain current due to the reduced gate voltage.

FIG. 6 shows the concentration curve of the EGFET device from 1 picomolar (pM) to 100 nanomolar (nM) cortisol concentration versus the current measured at a $V_{ds}$ of 5 V and a $V_{gs}$ of 5 V. This figure shows the concentration curve for cortisol as plotted from the $V_d$ versus $I_d$ data obtained in FIGS. 4 and 5. Drain current values at 5 volts were chosen and plotted against their respective concentration. The resulting exponential fit line is represented by the equation $(x)=a \times e^{(b \times x)}$, where $a=2.324 \times 10^{228}$, and $b=-1.052 \times 10^5$ with an R-square value of 0.9956.

FIG. 7 shows a plot of drain-source current versus gate voltage of the EGFET-MIP device at different cortisol concentrations. The drain voltage was kept as 1V. FIG. 8 shows a plot of the effective impedance versus the cortisol concentration (molar) on a logarithmic scale. FIGS. 5 and 6 show a decrease in drain current can be observed as cortisol concentration increases, and FIG. 8 shows that an increase in the impedance of the MIP extended gate can be observed at the same time. The cortisol molecules occupy the empty sites in the polymer matrix, and the occupation of conductive sites by cortisol causes a change in the interaction of charge carriers with the polymer surface. The change in surface charges restricts the flow of current across the MIP thin film via an increase in impedance. The reduced current, in effect, decreases the electron density in the gate region of the n-type MOSFET working in enhancement mode. This change in drain current due to increased cortisol concentration is used for sensing purposes.

The results show that systems and methods of embodiments of the subject invention can be used POC sensing of cortisol (a vital steroid biomarker for detection of stress). Not only is the MIP-EGFET sensor much faster than alternatives (<1 minute), but it is also simple to use, label free, and provides a direct readout. The molecularly imprinted technique is a promising technique for bio-sensing application, and the selectivity of the MIP can be improved by computationally exploring the interaction between the polymer and the bio-analyte. Also, simulation studies of different binding sites at the polymer can be useful for better understanding of loading/elution mechanisms of the target molecule/analyte (e.g., computationally exploring the energy required for effective removal of the target molecule without affecting the molecular backbone). At the device end, the EGFET configuration can be incorporated with miniaturized electronics to provide a direct readout in handheld or wearable device form and integrated with MIP based sensing electrodes.

TABLE 1

MIP-EGFET sensor compared to common sensing systems

| | SAM-based Sensing | MIP based sensing | MIP-EGFET sensor |
|---|---|---|---|
| Sensing Element | Monoclonal Antibodies | MIP | MIP |
| Detection Mode | CV | CV | EGFET |
| Label-free | No | Yes | Yes |
| Reusable | No | Yes | Yes |
| Selectivity | Yes | Yes | Yes |
| Limit of detection | 10 pg/mL | 0.0004 pg/mL | 0.0004 pg/mL |
| Direct readout | No | No | Yes |

The polypyrrole-based selective and validated MIP cortisol sensing chip was configured with an FET as an extended gate. The developed sensor was characterized and various concentrations of cortisol were detected using optimized pH and gate voltage. The device detected cortisol concentrations ranging from 1 pM to 100 nM and exhibited a detection range of 1 pM. Such a sensor provides label-free, fast, low-cost and direct sensing of cortisol. Due to the involvement of simple electronics and easy fabrication, a miniaturized cortisol sensing device can be used for POC applications.

Example 2

A screen printed carbon electrode (SPCE) was used to fabricate an MIP with cortisol selectivity, as with Example 1. The SPCE was a three-electrode system with an Ag/AgCl reference and two carbon electrodes. The thiol based cross-linker DTSP, and $NaBH_4$ were purchased from Thermo Fisher Scientific. Copper (II) Chloride ($CuCl_2$), KCl, and NaOH were obtained from Sigma Aldrich and used for deposition of copper nanoparticles. The buffer solution used for characterization was prepared from $NaH_2PO_4$ and $Na_2HPO_4$. These chemicals were also purchased from Sigma Aldrich. All the chemicals were of analytical grade and were used without further purification. The SPCE was combined with a commercially available FET for further experiments.

The MIP electrode was connected to the gate of the FET sensor, as shown in FIG. 1. The gate of the FET was connected to the working electrode of the SPCE. The gate voltage source was connected to the reference electrode of the SPCE. The source was grounded, and the drain was connected to the power source. The output and transfer characteristics of the FET were measured using the Keithley 4200 source meter. The output and transfer characteristics were measured by connecting the gate directly to the gate voltage ($V_g$) power supply and varying the gate voltage. After establishing the baseline measurements of the transistor, measurements were made with 50 μL of PBS with different pH values. Subsequent measurements were made in the PBS solution (7.6 pH) after incubating different cortisol concentrations on the MIP-modified, extended gate. The results were the same as those shown in FIG. 3.

Cortisol stock solution was prepared by dissolving lyophilized cortisol powder in ethanol and the PBS solution of pH of about 7.4. The stock solution was then diluted to obtain different cortisol concentrations. The MIP modified electrode was incubated with 10 uL of cortisol for 30 minutes. It was then washed away with deionized water and dried with nitrogen. 50 uL of PBS was then dispensed on the electrode, and the current-voltage measurements were made. FIGS. 9 and 10 show the output characteristics of different cortisol concentrations immobilized on the MIP modified, extended gate. The drain-source voltage was swept while the gate voltage was kept at 5 V (FIG. 9) and 1 V (FIG. 10).

FIG. 11 shows the concentration curve for cortisol as plotted from the $I_d$ versus $V_d$ data obtained in FIG. 10. Drain current values at 2 V were chosen and plotted against their respective concentration on a logarithmic scale.

As with Example 1, the device detected cortisol concentrations ranging from 1 pM to 100 nM and exhibited a detection range of 1 pM. Such a sensor provides label-free, fast, low-cost and direct sensing of cortisol. Due to the involvement of simple electronics and easy fabrication, a miniaturized cortisol sensing device can be used for POC applications.

It should be understood that the examples and embodiments described herein are for illustrative purposes only and that various modifications or changes in light thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A biosensing system for detecting a target biological analyte, the system comprising:
    a field effect transistor (FET) comprising a gate, a source, and a drain;
    an extended gate comprising a conductive substrate in electrical contact with the gate of the FET; and
    an external electrode that is not attached to the FET or the extended gate, configured to apply a gate voltage to a fluid disposed on a predefined area of the conductive substrate,
    the conductive substrate comprising a screen printed carbon electrode (SPCE) comprising a reference electrode and a working electrode,
    the extended gate being a single, continuous extended gate, and
    the reference electrode and the working electrode both being disposed on a same surface of the single continuous extended gate.

2. The biosensing system according to claim 1, the conductive substrate being a molecular imprinted polymer (MIP) that is specifically functionalized for the target biological analyte.

3. The biosensing system according to claim 1, the target biological analyte being cortisol.

4. The biosensing system according to claim 1, the external electrode being connected to a gate voltage source,
    the gate voltage source being connected to the reference electrode of the SPCE, and
    the gate of the FET being connected to the working electrode of the SPCE.

5. The biosensing system according to claim 1, the gate of the FET being connected to the working electrode of the SPCE.

6. The biosensing system according to claim 1, the drain of the FET being connected to a drain voltage source, and the source of the FET being grounded.

7. The biosensing system according to claim 1, the source of the FET being connected to a source voltage source, and the drain of the FET being grounded.

8. The biosensing system according to claim 1, the predefined area of the conductive substrate comprising a well in the conductive substrate configured to receive the fluid.

9. The biosensing system according to claim 1, further comprising:
    a small current amplifier in operable communication with the FET; and
    a microcontroller in operable communication with the small current amplifier,
    the microcontroller being configured to receive a source-drain characteristic and determine a concentration of the target biological analyte based on the source-drain characteristic, and
    the source-drain characteristic comprising at least one of a source-drain current and a source-drain voltage.

10. A method of sensing a concentration of a target biological analyte, the method comprising:
    providing a fluid comprising the target biological analyte to an extended gate comprising a single, continuous conductive substrate in electrical contact with the gate of a field effect transistor (FET), the FET comprising the gate, a source, and a drain;
    dipping an external electrode, which is not attached to the FET or the extended gate, in the fluid;
    providing a gate voltage to the external electrode via a gate voltage source connected to the external electrode;
    analyzing, by a controller in operable communication with the FET, a source-drain characteristic of the FET while the gate voltage is provided to the external electrode; and
    determining the concentration of the target biological molecule based on the source-drain characteristic of the FET,
    the source-drain characteristic comprising at least one of a source-drain current and a source-drain voltage,
    the conductive substrate comprising a screen printed carbon electrode (SPCE) comprising a reference electrode and a working electrode,
    the extended gate being a single, continuous extended gate, and
    the reference electrode and the working electrode both being disposed on a same surface of the single continuous extended gate.

11. The method according to claim 10, the conductive substrate being a molecular imprinted polymer (MIP) that is specifically functionalized for the target biological analyte.

12. The method according to claim 10, the target biological analyte being cortisol.

13. The method according to claim 10, the gate voltage source being connected to the reference electrode of the SPCE, and
    the gate of the FET being connected to the working electrode of the SPCE.

14. The method according to claim 10, the drain of the FET being connected to a drain voltage source, and the source of the FET being grounded.

15. The method according to claim 10, the source of the FET being connected to a source voltage source, and the drain of the FET being grounded.

16. The method according to claim 10, the fluid being provided to a predefined area of the conductive substrate, the predefined area comprising either: a) a well in the conductive substrate in which the fluid is deposited; or b) a flat area on an upper surface of the conductive substrate on which the fluid is deposited.

17. The method according to claim 10, in which a small current amplifier is in operable communication with the FET,
    the controller being a microcontroller in operable communication with the small current amplifier.

18. A method of sensing a concentration of a target biological analyte, the method comprising:

providing a fluid comprising the target biological analyte to an extended gate comprising a single, continuous conductive substrate in electrical contact with the gate of a field effect transistor (FET), the FET comprising the gate, a source, and a drain;

dipping an external electrode, which is not attached to the FET or the extended gate, in the fluid;

providing a gate voltage to the external electrode via a gate voltage source connected to the external electrode;

analyzing, by a controller in operable communication with the FET, a source-drain characteristic of the FET while the gate voltage is provided to the external electrode; and determining the concentration of the target biological molecule based on the source-drain characteristic of the FET, the source-drain characteristic comprising at least one of a source-drain current and a source-drain voltage, the conductive substrate being a molecular imprinted polymer (MIP) that is specifically functionalized for the target biological analyte, the target biological analyte being cortisol, the conductive substrate comprising a screen printed carbon electrode (SPCE) comprising a reference electrode and a working electrode, the gate voltage source being connected to the reference electrode of the SPCE, the gate of the FET being connected to the working electrode of the SPCE, the fluid being provided to a predefined area of the conductive substrate, the predefined area comprising either: a) a well in the conductive substrate in which the fluid is deposited; or b) a flat area on an upper surface of the conductive substrate on which the fluid is deposited, the controller being a microcontroller in operable communication with a small current amplifier that is in operable communication with the FET the extended gate being a single, continuous extended gate, and the reference electrode and the working electrode both being disposed on a same surface of the single, continuous extended gate.

* * * * *